US011844348B2

United States Patent
Cope et al.

(10) Patent No.: US 11,844,348 B2
(45) Date of Patent: *Dec. 19, 2023

(54) POLLEN PRESERVATION AND STORAGE METHOD

(71) Applicant: Accelerated Ag Technologies, LLC, Ames, IA (US)

(72) Inventors: Jason Cope, Ankeny, IA (US); George Singletary, Ankeny, IA (US); Todd Krone, Des Moines, IA (US); Sara Katherine Etter, Bondurant, IA (US)

(73) Assignee: Accelerated Ag Technologies, LLC, Ames, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/686,939

(22) Filed: Mar. 4, 2022

(65) Prior Publication Data

US 2022/0192183 A1 Jun. 23, 2022

Related U.S. Application Data

(63) Continuation of application No. 16/803,565, filed on Feb. 27, 2020, now Pat. No. 11,344,027, which is a continuation of application No. 15/486,737, filed on Apr. 13, 2017, now Pat. No. 10,575,517, which is a continuation-in-part of application No. 15/192,519, filed on Jun. 24, 2016, now Pat. No. 10,398,099.

(60) Provisional application No. 62/321,914, filed on Apr. 13, 2016, provisional application No. 62/269,496, filed on Dec. 18, 2015, provisional application No. 62/269,531, filed on Dec. 18, 2015, provisional application No. 62/269,514, filed on Dec. 18, 2015, provisional application No. 62/184,596, filed on Jun. 25, 2015.

(51) Int. Cl.
*A01N 3/00* (2006.01)
*A01G 7/00* (2006.01)

(52) U.S. Cl.
CPC ............... *A01N 3/00* (2013.01); *A01G 7/00* (2013.01)

(58) Field of Classification Search
None
See application file for complete search history.

(56) References Cited

FOREIGN PATENT DOCUMENTS

| CA | 966734 | 4/1975 |
| SU | 1061770 | 12/1983 |
| WO | 2013070846 | 5/2013 |

OTHER PUBLICATIONS

Mexican Direccion Divisional de Patentes, Office Action dated Jul. 28, 2022, Application No. MX/a/2017/017162.
Canadian Patent Office, Application No. 2,990,424 Office Action, dated Dec. 8, 2021.
Chile Presentado Por Sistema De Gestion De Peritos Internet, Application No. 201703348, Office Action, dated Sep. 10, 2019.
Chinese Patent Office, Application No. 201680049186.7, 3rd Office Action, dated Jan. 12, 2022.
European Patent Office, Application No. 16 739 302.4-1120, Office Action, dated Dec. 13, 2019.
European Patent Office, Application no. 16 739 302.4-1118, Office Action, dated Jan. 29, 2021.
European Patent Office, Application No. 16 739 302.4-1118, Office Action, dated Sep. 23, 2021.
Direccion Divisional De Patentes (Mexico), Application No. Mx/a82017/017156, Office Action, dated Mar. 4, 2022.
Brazilian Federal Public Service Ministry of Economy, National Institute of Industrial Property, Application No. BR112017028054-0, dated May 17, 2023.
Russian Federation Federal Service for Intellectual Property, Application No. 2018102578/10, Office Action dated Feb. 15, 2023.
Brazilian Federal Public Service Ministry of Economy, National Institute of Industrial Property, Application No. BR112017028059-0, dated May 16, 2023.
Russian Federation Federal Service for Intellectual Property, Application No. 2018102577/10, Office Action dated May 26, 2023.
Indian Patent Office, Application No. 201837037257, Office Action dated Jul. 7, 2023.
Canadian Innovation, Sciences and Economic Development Canada, Application No. 3,020,871, Office Action dated Mar. 22, 2023.
European Search Report, Application No. EP22 19 7797.8-1118 dated Mar. 23, 2023.
Innovation, Science and Economic Development Canada, Application No. 2,990,424, Office Action dated Dec. 20, 2022.
Resolucion de correcciones de forma Chile, Office Action, Application No. 201703348 dated Nov. 29, 2022.
Innovation, Science and Economic Development Canada, Application No. 2,990,423, Office Action dated Nov. 25, 2022.
European Patent Office, Communication pursuant to Article 94(3) EPC, Application No. 16 738 296.9-1118, dated Feb. 8, 2023.
Servico Publico Federal Brazil, Office Action, Application No. BR112018071134-9, dated Jan. 6, 2023.
Resolucion de correcciones de forma Chile, Office Action, Application No. 201802926, dated Dec. 23, 2022.
European Communication pursuant to Article 94(3) EPC, Application No. 16 738 396.9-1118, dated Feb. 8, 2023.

(Continued)

*Primary Examiner* — Medina A Ibrahim
(74) *Attorney, Agent, or Firm* — Brick Gentry Law Firm; Brian J. Laurenzo

(57) ABSTRACT

Described are methods of preserving cereal crop pollen and/or anthers. A method of the present invention includes collecting fresh pollen and/or anthers and introducing the pollen and/or anthers to field conditioning conditions which regulate pollen moisture content. The field conditioning conditions may include a an air flow at a humidity ranging from 0% to about 99% and a temperature ranging from about −10-10° C. The field conditioning conditions may further include a flow of one or more continuously refreshed, selected gases. The field conditioning conditions may dehydrate the pollen to achieve a pollen moisture content of about 15% to about 35%.

22 Claims, 18 Drawing Sheets

(56) References Cited

OTHER PUBLICATIONS

Canadian Patent Office, Application No. 3,020,871, Office Action dated Mar. 22, 2023.
European Communication pursuant to Article 94(3) EPC, Application No. 17 718 712.7-1118, dated Feb. 28, 2023.

POLLEN PRESERVATION AND STORAGE METHOD

CROSS REFERENCE TO RELATED APPLICATIONS

This application is a continuation of U.S. patent application Ser. No. 16/803,565, filed Feb. 27, 2020 and entitled "Cereal Crop Pollen Field Conditioning". U.S. patent application Ser. No. 16/803,565 is a continuation of U.S. patent application Ser. No. 15/486,737, filed on Apr. 13, 2017 and entitled "Pollen Field Conditioning and Preservation Method", now U.S. Pat. No. 10,575,517 issued Mar. 3, 2020. U.S. patent application Ser. No. 15/486,737 is a continuation-in-part of U.S. Non-Provisional patent application Ser. No. 15/192,519, filed on Jun. 24, 2016 and entitled "Grain Production", now U.S. Pat. No. 10,398,099 issued Sep. 3, 2019, which claims priority from U.S. Provisional Application Ser. No. 62/184,596 filed Jun. 25, 2015 and entitled SEED PRODUCTION and from U.S. Provisional Application Ser. No. 62/269,496 filed Dec. 18, 2015 and entitled SEED PRODUCTION and from U.S. Provisional Application Ser. No. 62/269,531 filed Dec. 18, 2015 and entitled GRAIN PRODUCTION and from U.S. Provisional Application Ser. No. 62/269,514 filed Dec. 18, 2015 and entitled GRAIN PRODUCTION. U.S. Non-Provisional patent application Ser. No. 15/486,737 claims priority from U.S. Provisional Application No. 62/321,914 filed Apr. 13, 2016 and entitled POLLEN CONDITIONING AND STORAGE METHOD. The contents of United States Non-Provisional patent application Ser. Nos. 16/803,565; 15/192,519; and 15/486,737 and Provisional Application Ser. Nos. 62/184,596; 62/269,496; 62/269,531; 62/269,514; and 62/321,914 are hereby incorporated in their entireties by reference.

This invention was made with government support under USDA SBIR Phase 1 Award No. 2016-33610-25366 titled Development of Rigorous and Reliable Methods to Preserve Maize Pollen awarded by the United States Department of Agriculture (USDA). The government has certain rights in the invention.

FIELD OF THE INVENTION

This invention relates generally to a novel pollen field conditioning and preservation method for increasing the overall viability and fertility of pollen for use in making pollinations conducted with either fresh pollen or pollen that has been preserved.

BACKGROUND

The current invention has application to the field of pollen longevity and viability. Pollen longevity varies significantly among species and is significantly influenced by environmental conditions, most notably temperature and relative humidity. Pollen, which is naturally shed from the flowers or flowering structures of angiosperms, is subject to rapid loss of viability once it is shed from the plant. Viability can be lost in minutes to hours depending on species and environmental conditions. Exposure to dry air and high temperature is particularly detrimental to pollen viability and longevity once it is shed from the plant. Thus, under natural field conditions, pollen has a limited lifespan during which it remains viable, referred to in this application as the "viability window." In particular, pollen from the Poaeceae (Gramineae) family of plants, commonly referred to as grasses, is particularly vulnerable and short-lived (Barnabas & Kovacs (1997) In: *Pollen Biotechnology For Crop Production And Improvement*. (1997). Sawhney, V. K., and K. R. Shivanna (eds). Cambridge University Press. pp. 293-314). This family of plants includes many economically important cereal crops, including maize. Methods to improve pollen viability and extend the duration of its viability are of significant value to the agricultural industry.

Specifically, if pollen collected from plants can be stored in a viable state for a period of time, this pollen may be used to pollinate female flowers as desired in a number of advantageous ways. Utilizing stored pollen allows for pollination which is not dependent on active pollen shed, temporal synchrony with pistil (female flower) receptivity, use of male sterility, and/or physical isolation from other pollen sources. Currently, many species rely on self-pollination or cross pollination by neighboring plants to produce fertile seed or grain. Typically in the agricultural hybrid seed industry, mechanical, physical, and/or genetic interventions are required to ensure female plants are cross pollinated, and not self-pollinated, so that pollen of a specific genetic constitution is employed to produce hybrid seed. Such measures, for example, are used routinely to produce hybrid maize and rice seed. In some crops, however, even these measures are not effective to ensure cost-effective cross pollination by a specific desired pollen source. Currently, it is not possible, or is very difficult to, produce these crops commercially as hybrids. Examples of these crops include, but are not limited to, wheat and soy.

Many attempts have been made to preserve pollen and extend its viability for pollinations beyond the time the pollen would remain viable if left exposed to uncontrolled ambient conditions. Among the grasses, studies with maize are exemplary of the progress made in pollen preservation. Many types of treatments have been tested for maintaining or extending maize pollen viability and/or fertility. Among them, the favorability of treating and/or storing maize pollen at high humidity and/or cold temperature has been reported by many.

Among the earliest accounts of maize pollen preservation (Andronescu, Demetrius I., The physiology of the pollen of *Zea mays* with special regard to vitality. Thesis for degree of Ph.D. University of Illinois. 1915), it was reported that in the absence of controlled environmental storage conditions, pollen died in two to four hours. By raising the relative humidity of the storage environment, the pollen's viability was maintained for 48 hours. Moreover, storage at low temperature (e.g., 8-14° C.) had a stimulative effect upon the viability of the pollen.

Even when relative humidity is not controlled during storage, maize pollen held at low temperature (e.g., 2-7° C. for 3-120 hours) can more than double its in vitro germinability compared to initial, pre-storage vitality or compared to storage at 35° C. (Pfahler, P. L. and Linskens, H. F., (1973) *Planta*, 111(3), pp. 253-259; Frova, C. B. and Feder, W. A., (1979) *Ann Bot*, 43(1), pp. 75-79). When high humidity (90% RH) and low temperature (4° C.) during storage are combined for pollen treatment, germination of maize pollen on artificial media remains good, to fair, for eight days (Sartoris, G. B., (1942) *Am J Bot*, pp. 395-400). Storage of maize pollen under the same conditions for eight days also allows the pollen to remain fertile, albeit at a reduced level, and capable of forming kernels on ears following pollination (Jones, M. D. and Newell, L. C., (1948) *J Amer Soc Agron* 40:195-204).

Field conditioning maize pollen at high humidity and low temperature commonly help revive pollen of low viability and/or extend its longevity, whereby at least limited seed formation occurs following pollination of ears. But the stimulative effect of low temperature storage on fertility is not always observed (Walden, D. B., (1967) *Crop Science,* 7(5), pp. 441-444) and if the pollen becomes dehydrated to excessive levels, pollen tube formation on artificial media and silks can be markedly reduced (Hoekstra, F A. (1986) In: *Membranes, Metabolism and Dry Organisms.* (Ed., AC Leopold), pp. 102-122, Comstock Publishing Associates, Ithaca, N.Y.; Barnabas, B. and Fridvalszky, L., (1984) *Acta Bot Hung* 30:329-332).

Although high humidity and low temperature slow the temporal decay of viability during storage of Gramineae pollen, optimizing these environmental conditions for preservation only postpones the complete loss of viability and fertility. Methods in addition to regulating humidity and temperature are needed to further enhance the longevity of stored pollen so that it can be used in commercial practice of supplemental pollination for improved seed and grain production.

In some cases, it may be desirable to treat pollen so that it is dehydrated to various degrees. Dehydration can be achieved by vacuum drying or exposing pollen to a relative humidity and temperature (i.e., vapor pressure deficit) that causes water to diffuse out of the pollen. Vapor pressure deficits favorable for pollen drying can be produced in a number of ways, such as with desiccants, mechanical equipment designed to control temperature and relative humidity in an enclosed chamber and with saturated salt solutions held in a closed space (Jackson, M. A. and Payne, A. R. (2007) *Biocontrol Sci Techn,* 17(7), pp. 709-719), Greenspan, L., (1977) *J Res Nat Bur Stand,* 81(1), pp. 89-96)

In an effort to dehydrate and preserve sugarcane pollen, the pollen was stored at low temperature under vacuum with a small amount of $CaCl_2$) desiccant present (Sartoris, G. B. (1942) *Am J Bot,* pp. 395-400). The pollen remained dry throughout storage, as desired, but use of low pressure was not as favorable as storage at normal atmospheric pressure. The behavior of corn pollen was very similar to that of sugarcane. More direct attempts at dehydration have incubated pollen in conditions of established or recorded relative humidity and temperature. These examples show that maize pollen can be dehydrated to very low levels (e.g., 7-10% pollen water content) and still possess an ability, albeit reduced, to effect seed formation following pollination of ears (Barnabas, B., et al. (1988) *Euphytica,* 39(3), pp. 221-225; U.S. Pat. No. 5,596,838).

Dehydration of pollen is commonly performed ahead of freezing for storage and preservation at very low temperatures. As practiced with maize, fresh pollen is dehydrated at room temperature in a vacuum chamber, humidity incubator, or simply with air-drying or mild heat (U.S. Pat. No. 5,596,838; Barnabas, B. and Rajki, E. (1981). *Ann Bot,* 48(6), pp. 861-864; Connor, K. F. and Towill, L. E. (1993) *Euphytica,* 68(1), pp. 77-84). Upon thawing after short or long term storage, cryopreserved pollen can be viable and fertile, but fertility is not always exhibited and some members of the Gramineae family, such as maize, sorghum, oat and wheat, can be difficult to cryopreserve (Collins, F. C., et al. (1973) *Crop Sci,* 13(4), pp. 493-494). One explanation offered for this recalcitrance is excess drying or aging of the pollen (Collins, F. C., et al. (1973) *Crop Sci,* 13(4), pp. 493-494). It is evident that pollen quality can be affected by prevailing environmental conditions during floral development, pollen maturation, and anthesis (Shivanna, K. R., et al. (1991) *Theor Appl Genet* 81(1), pp. 38-42; Schoper, J. B., et al. (1987) *Crop Sci,* 27(1), pp. 27-31; Herrero, M. P. and Johnson, R. R. (1980) *Crop Sci,* 20(6), pp. 796-800). Pollen stressed in these ways could exhibit a reduced propensity to withstand the rigors of dehydration and freezing for cryopreservation. A need exists to overcome this problem and make cryopreservation of Gramineae pollen more attainable and routine so this form of pollen preservation can be implemented in a predictable way on a commercial scale.

Desiccation is known to have a direct impact on pollen viability. Barnabas (1985) *Ann Bot* 55:201-204 and Fonseca and Westgate (2005) *Field Crops Research* 94: 114-125 demonstrated that freshly harvested maize pollen could survive a reduction in original water content of approximately 50%, but few pollen grains demonstrated viability or a capacity for normal pollen tube formation with an additional water loss beyond that level. Early work by Barnabas and Rajki ((1976), *Euphytica* 25: 747-752) demonstrated that pollen with reduced water content would retain viability when cryogenically stored at −196° C. Subsequent work (Barnabas & Rajki (1981) *Ann Bot* 48:861-864) demonstrated that such partially-desiccated maize pollen grains stored at −76° C. or −196° C. also could effect fertilization of receptive female flowers. Other methods of storing pollen for varying periods of time are known in the art, including freeze-drying, vacuum-drying, and storage in organic non-polar solvents. Limitations in the scalability of these pollen preservation techniques combined with the complex, non-portable equipment requirements render these techniques impractical for use with large volumes of pollen required for field-scale applications.

U.S. Pat. No. 5,596,838 from Greaves, et al., discloses a method of storing pollen that involves a reduction in moisture level by exposing pollen to reduced atmospheric pressures prior to storage. This technique prepared small quantities of pollen, such as from a single maize plant, for subsequent storage under sub-zero conditions. The Greaves et al. method has drawbacks. For example, the methodology and mechanical system requirements lack the capacity to produce stored pollen in quantities large enough to enable commercial seed production or grain production applications. These requirements effectively negate any opportunity to advance the technology beyond research level investigations. For example, the ability to create a vacuum chamber large enough for production-level field pollination preservations would require a very large vacuum chamber capable of rapidly changing pressure levels. Production-level parent increase fields are typically an acre or more, while hybrid production fields are typically 10 acres or more in size. Such fields require a considerable amount of pollen and thus a large vacuum chamber would be needed. A chamber of the Greaves, et al. specifications would require the ability to pump down to a pressure of 5 Torr (0.67 kPa) or less, with the added ability to rapidly up cycle and down cycle this level of pressure. As the physical volume of the sample increases, the ability to generate and cycle at 5 Torr (0.67 kPa) efficiently begins to go beyond what mechanical pumps can generate. In addition, storage of pollen in organic solvents creates hazardous chemical requirements.

The availability of preserved, viable pollen would overcome many of the production challenges faced by the hybrid seed industry. As provided in further detail in Applicant's U.S. patent application Ser. No. 15/192,485, the entire contents of which are hereby incorporated by reference, with respect to hybrid seed, the availability of stored pollen for delivery to female flowers can eliminate many standard, costly practices of seed production including, but not limited to, planting male plants in proximity to female plants to enable hybridization, isolation of female plants from undesired pollen sources, and use of genetic or mechanical male sterility of the female plants. These practices dramatically increase field space and resources dedicated to female plants which produce seed or grain. Reducing or eliminating any one of these practices would reduce the cost of hybrid seed production. Moreover, stored pollen can be applied at any time. When pollen shed from male plants and pollen receptivity of female plants fail to coincide as planned (due to management, environment, or genetic variation), application of preserved, viable pollen can ensure pollination of female plants at the optimal time. Pollination by undesired external (adventitious) sources of pollen or undesired self-pollination of female plants also can be reduced or eliminated by applying stored pollen of a desired type at the appropriate time. Today, the genetics of a particular hybrid seed is determined at the beginning of a growing season by the genotype of the pollen-donating male plants and pollen-receiving female plants planted together in the field. Using the embodiments of the present disclosure, however, a hybrid seed producer responding to changing market opportunities can decide at the time of pollination to use a different male pollen (i.e., genetic source) for pollination to produce more valuable hybrid seed. In addition, stored pollen can be used to deliver unique genetic traits or genes that enhance seed quality characteristics to highly productive female inbreds. For example, traits for resistance to select insect pests which are present might be delivered. Importantly, the embodiments of the present disclosure also ensure a high level of genetic purity in the hybrid seed. As such, methods of improving pollen viability for multiple crop species and extending the duration of its viability are of significant value to the agricultural industry.

SUMMARY OF THE INVENTION

Figure 1:
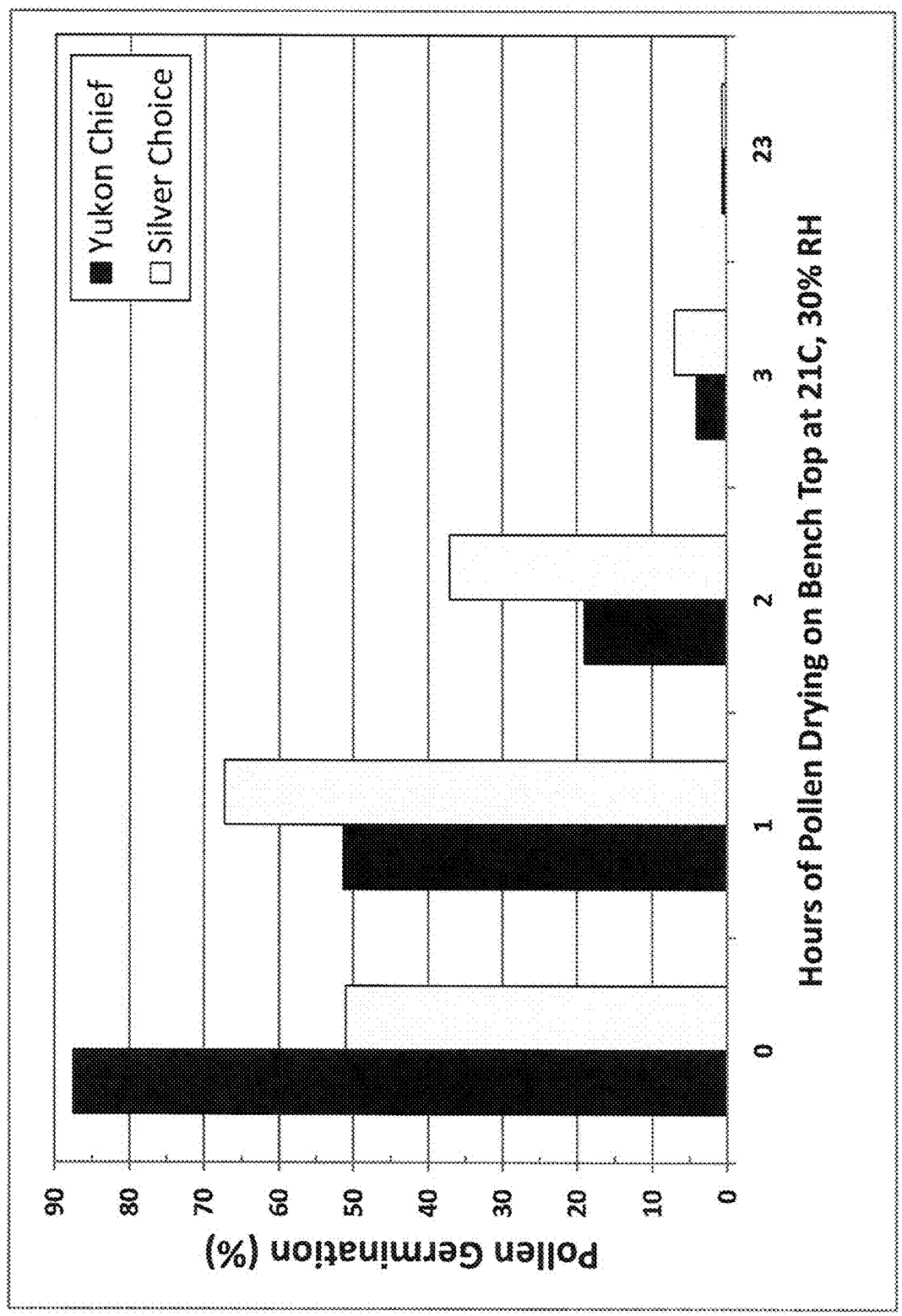
FIG. 1: This figure demonstrates the effect of ambient laboratory conditions of 21° C. and 30% relative humidity on the viability of freshly-shed pollen over time.

Provided is a method of preserving pollen from cereal crops comprising collecting pollen and/or anthers, subjecting the pollen and/or anthers to preservation conditions, and storing the pollen and/or anthers for future use. The preservation conditions include a temperature ranging from about −10° C. to about 10° C. and an air flow at a humidity of 0% to 99%, wherein the air pressure is capable of adjustment and the pollen is dehydrated until the pollen moisture content reaches about 15% to about 35%.

The air flow may include a flow of one or more continuously refreshed, selected gases. The gas may be nitrogen gas having a concentration of about 78% to about 100%. Moreover, the air flow humidity level may be controlled by using a saturated salt solution, a two-pressure process, a two-temperature process, or one or more apparatuses. The apparatuses may be a dew-point generator, an atomizer, a mixed-flow generator, and/or a sonicator.

The pollen and/or anthers may be freshly collected from actively shedding plants, or the pollen and/or anthers may have been previously collected and stored. Pollen may be collected from anthers by crushing, grinding, or otherwise disrupting the anther in order to obtain the pollen therefrom. The pollen and/or anthers may be maize, rice, or wheat pollen. Storage of the pollen may be at −80° C. to −30° C., −30° C. to −10° C., −10° C. to 10° C., or 10° C. to 40° C.

In another embodiment of the invention pollen and/or anthers are collected, subjected to preservation conditions, and stored. The preservation conditions include a temperature ranging from about −10° C. to about 10° C. and a flow of nitrogen at a humidity of 0% to about 99%, wherein the humidity is capable of adjustment and the pollen is dehydrated until the pollen moisture content reaches about 15% to about 35%.

The nitrogen flow humidity level may be controlled by using a saturated salt solution, a two-pressure process, a two-temperature process, or one or more apparatuses. The apparatuses may be a dew-point generator, an atomizer, a mixed-flow generator, and/or a sonicator.

The pollen and/or anthers may be freshly collected form actively shedding plants, or the pollen and/or anthers may have been previously collected and stored. Pollen may be collected from anthers by crushing, grinding, or otherwise disrupting the anther in order to obtain the pollen therefrom. The pollen and/or anthers may be maize, rice, or wheat pollen. Storage of the pollen may be at −80° C. to −30° C., −30° C. to −10° C., −10° C. to 10° C., or 10° C. to 40° C.

DETAILED DESCRIPTION

The following is a detailed description of an embodiment of technology and methods enabling improved and extended viability of collected pollen, including techniques of field-conditioning pollen and subjecting it to specialized preservation techniques. The pollen may be collected from actively shedding plants or, alternately, the pollen to be field conditioned may have been previously collected and stored according to numerous methods known in the art that maintain pollen viability over a period of time. Such methods include, for example, freezing, freeze-drying, storing in liquid nitrogen, etc.

In order to field condition pollen for improved and extended viability, the pollen is maintained in, or transferred to, a storage chamber that permits the modification and/or maintenance of changes to one or more of relative humidity, temperature, atmospheric pressure, and gaseous component concentrations of the atmosphere present in the chamber. For the purposes of this invention, the term "chamber" is used to mean an enclosure suitable for containing and storing pollen. A chamber can vary in size and material of construction. The chamber may be of any size that is suitable for containing a quantity of pollen, and may be any kind of container, vessel, enclosure, or space in which pollen is being stored, wherein the space serves as a chamber for the storage of large quantities of pollen. In all cases, the chamber must be one in which the environmental conditions can be regulated for selected parameters such as, but not limited to, temperature, relative humidity, composition of gases, and pressure. The chamber may be equipped with a vent or other means to allow pressure to escape from the system and to allow moisture removed from the pollen to be removed from the chamber.

For the purposes of this disclosure, the term "viable" or "viability" is used to describe pollen that is able to germinate and grow a pollen tube to at least a length twice the diameter of the pollen grain. In addition, pollen can be judged viable by demonstration that the cellular nature of the material remains integral and is judged to maintain intactness such that normal cellular processes of metabolism and intracellular functioning is possible. The viability of pollen can be assessed in numerous ways, including, but not limited to, assessment of pollen tube growth on artificial media or excised stigmas or styles, assessment of cellular intactness by vital staining of numerous sorts, absence of electrolyte (e.g., potassium) leakage, and impedance flow cytometry. Viable pollen can successfully germinate and commonly possesses the vigor necessary to promote fertilization and initiation of seed development. Not all viable pollen is also fertile pollen. In some cases, even when a pollen grain is viable and commences with pollen tube growth, it may lack the vigor necessary to reach the ovule and promote fertilization. Non-viable pollen grains cannot successfully germinate. Viability can refer to a single pollen grain or a population of pollen grains. When a percentage value is used to describe pollen viability, the value is typically being applied to a population of pollen.

Another term that can be used to describe the ability of pollen to germinate and form the pollen tube is "germinability." Thus, pollen with good viability is pollen that is desirable for use with the methods in the present disclosure. The "viability window" refers to the limited lifespan during which pollen remains viable.

For the purposes of this disclosure, the term "fertile" or "fertility" is used to describe the ability of pollen to deliver the sperm nuclei to the ovule and thereby effect double fertilization. In flowering plants, the term "double fertilization" refers to one sperm nucleus fusing with the polar nuclei to produce the endosperm tissues, and the other sperm nucleus fusing with the egg nucleus to produce the embryo.

For the purposes of this disclosure, "loss of viability" and "loss of fertility" are terms used to describe pollen. These terms mean, respectively, that the viability and fertility of the pollen has fallen to a level below that required for successful initiation of seed development. The level of viability and fertility required for successful pollinations is typically defined to be an average of 4 grains of fresh pollen per ovule, or 4 to 8 grains of preserved pollen which has been preserved according to the methods of the present disclosure.

For the purposes of this disclosure, the term "longevity" is used to describe the length of time that pollen remains both viable and fertile.

For the purposes of this disclosure, the term "pollen field conditioning" or "field conditioning" is used to describe the process disclosed in this application of treating freshly-collected pollen in the field to maintain or improve its viability, allowing for more successful pollen storage. Storage success is measured by the percentage of a population of pollen that remains both viable and fertile throughout a period of storage. Field conditioning typically takes place in the field where the pollen is being collected, such that the field conditioning is conducted prior to transporting the pollen to a laboratory or other location. It is an immediate process that is conducted upon the gathering of the pollen. Field conditioning may also take place in other locations where plants are grown and where pollen collection takes place, such as a growth chamber, a greenhouse, a glasshouse, a shade house, a hoop house, a vertical farming facility, a hydroponic facility, or any growing facility providing cultured tassels, as described below. Field conditioning includes any intentional regulation of environmental conditions (e.g., relative humidity, temperature, gaseous composition, pressure, light, etc.) of a confined space in which freshly-collected pollen is held immediately following its collection and prior to transportation to any other location. Periods of field conditioning can be brief, on the order of minutes to hours, or extended up to several days. The term "revive" or "revival" is used to describe the nature of the pollen during the field conditioning process. For example, to "revive" pollen during the field conditioning process may include improving one or more of the viability, germinability, or fertility of the pollen.

For the purposes of this disclosure, the term "storage" means any period of pollen containment with the intent of using the pollen at a later time or date. The term "preservation" means any storage of pollen that results in a level of viability, fertility, or both, which is different than the level of viability, fertility or both, which would occur if the pollen were held in unregulated ambient environmental conditions. Pollen may, optionally, be field-conditioned prior to storage or preservation.

For the purposes of this disclosure, the term "female plant" is used to mean a plant that is being used as the recipient of the pollen, and which has receptive flowers that are being fertilized. In the case of maize, and many other species, the plant is monoecious and contains male and female inflorescences on a single plant. In the practice of breeding, pollination, cross-pollination, and hybridization, some plants act as the "male plant" from which pollen is collected for use in pollinations, and some plants act as the "female plant" being the recipient of the pollen. In the case of self-pollinations, a single plant is acting as both the "male plant" and the "female plant" because the female flowers are fertilized by pollen from its own male flowers.

For the purposes of this disclosure, the term "fresh" when applied to pollen means pollen released from the anthers of a flower which, in its natural pattern of organ growth and development, releases pollen upon dehiscence in response to promotive environmental conditions.

The collection of fresh pollen may be conducted in ways commonly known in the art. For example, pollen may be collected from freshly shedding flowers or male flower structures produced in any variety of manners. In the case of maize, for example, pollen is collected from freshly-shedding male flowers borne on tassels, which may be attached, or detached, from the plant. The pollen may be collected from plants grown in any environment suitable for plant growth. Such environments include, but are not limited to, a field, a growth chamber, a greenhouse, a glasshouse, a shade house, a hoop house, a vertical farming facility or a hydroponic facility. Alternatively, pollen may be collected directly from anthers by crushing or grinding the anthers, thereby releasing the pollen and allowing for its collection. In addition, pollen may be collected from a tassel culture facility (Pareddy D R, Greyson R I, Walden D B (1989) Production of normal, germinable and viable pollen from in vitro-cultured maize tassels. Theor Appl Genet 77:521-526). Cultured tassels may be mature tassels that have been removed from plants in any type of growing facility or environment, including a field or other type of growing facilities, and placed into water in a controlled environment to collect pollen or cultured tassels may be tissue that has been harvested from flowering structures at immature stages and then cultured to develop into a fully mature flowering structure or tassel.

Field conditioning and storage of pollen may be achieved through placement of the material into a chamber where environmental conditions are regulated. For example, a refrigeration chamber with controlled temperature and the ability to control relative humidity could be used to field condition and/or preserve the collected pollen. The unit would also have an inlet for flushing various gases or mixtures of gases, such as nitrogen, carbon dioxide, and/or oxygen, into the chamber. Likewise, a room suitable for storing larger volumes of pollen, which is supplied by a mechanical form of humidification (sonic, ionized, etc.), dehumidification, is temperature controlled, and permits sampling, monitoring and balancing of gases or gaseous mixture supply in the ambient air, is a chamber.

Pollen intended for field conditioning and subsequent preservation and storage is placed into an environment with high relative humidity, as indicated in various examples, including but not limited to example 4 which assesses the effect of relative humidity on the pollen. The relative humidity may be, for example, any value ranging from about 75% humidity to about 100% humidity, including about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, and about 100% humidity. At the same time, the environment must have a relatively low temperature, as provided in examples including, but not limited to Example 4. A relatively low temperature may be, for example, any value ranging from about −10° C. to about 10° C., including about −10° C., about −9° C., about −8° C., about −7° C., about −6° C., about −5° C., about −4° C., about −3° C., about −2° C., about −1° C., about 0° C., about 1° C., about 2° C., about 3° C., about 4° C., about 5° C., about 6° C., about 7° C., about 8° C., about 9° C. and about 10° C. Field conditioning is conducted at an air pressure ranging from about 15 kPa to about 150 kPa, including about 15 kPa, about 20 kPa, about 25 kPa, about 30 kPa, about 35 kPa, about 40 kPa, about 45 kPa, about 50 kPa, about 55 kPa, about 60 kPa, about 65 kPa, about 70 kPa, about 75 kPa, about 80 kPa, about 85 kPa, about 90 kPa, about 95 kPa, about 100 kPa, about 105 kPa, about 110 kPa, about 115 kPa, about 120 kPa, about 125 kPa, about 130 kPa, about 135 kPa, about 140 kPa, about 145 kPa, or about 150 kPa. The field conditioning environment may have a flow of one or more continuously refreshed, selected gases, wherein the gas displaces oxygen. Examples of such a field conditioning environment can be found in Example 11 and Example 12. It is anticipated that many gases may be used for this purpose, including but not limited to inert gases. In some embodiments, gases including nitrogen, carbon dioxide, or combinations thereof may be used. In one preferred embodiment, nitrogen gas may be used. Moreover, the concentration of nitrogen ($N_2$ gas) present in the chamber may be moderated from about atmospheric percentage to about 100%, including about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, and about 100% nitrogen. The concentration of oxygen ($O_2$ gas) present in the chamber may be moderated from about the prevailing atmospheric percentage to about 0%, including about 21%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, and about 0% oxygen.

When the pollen is in this environment with high relative humidity and relatively low temperature, it is being field conditioned. The period of field conditioning will enhance pollen health and viability. After field conditioning, the pollen may be subjected to further preservation techniques or it may be stored.

In order to achieve a known relative humidity level, a variety of means known in the art may be employed. These include, but are not limited to, using an apparatus such as a dew-point generator, an atomizer, a mixed-flow generator, a sonicator, or other apparatus designed to increase relative humidity. It can also be achieved using a two-pressure process, a two-temperature process, or a saturated salt solution. The two-pressure humidity generation process involves saturating air or nitrogen with water vapor at a known temperature and pressure. The saturated high-pressure air flows from the saturator, through a pressure reducing valve, where the air is isothermally reduced to test pressure at test temperature. Likewise, the two-temperature method circulates an air stream through a precise temperature controlled saturator (water spray or bubble column). The air becomes saturated at the temperature of the water. When leaving the saturator, the air travels through a mist elimination device to insure liquid water does not go beyond the saturator. The air is then reheated to the desired dry bulb temperature. The temperature of the saturator would equal the dew point temperature. RH is calculated from the dew point and dry bulb temperatures (two temperature method).

As shown in Example 1, freshly-collected maize pollen from eight diverse genetic backgrounds shows significant variation in viability, even when sampled on a single day under the same conditions. Pollen originating from diverse genetic backgrounds shows significant differences in ability to tolerate heat stress and vapor pressure deficits. Subsequent experimentation on pollen collected from two different genetic backgrounds (see Example 2) showed that freshly-shed pollen rapidly declines in its ability to germinate successfully when exposed to ambient laboratory conditions.

The loss of moisture impacts the viability of pollen, with greater moisture loss resulting in greater viability loss, and eventually the death of the pollen grain. The rate of moisture loss is dependent upon a number of factors, including, but not limited to, ambient temperature, relative humidity, and wind conditions. Pollen death occurs most quickly in hot, dry conditions, such as those conditions expected during a drought. Placing pollen which is losing moisture content into an environment which has high relative humidity and relatively low temperature allows the pollen to recover its moisture content almost to its pre-shed level, however, it does not completely stop the pollen from metabolic activity, which consumes vital resources. This is demonstrated in Example 3, which demonstrates improvement in pollen germination rates following field conditioning at high humidity and low temperature. Further experimentation demonstrated that field conditioning pollen at high humidity elevated low viability within one hour, but additional benefit was gained from field conditioning at low temperature.

The rate of moisture removal from pollen has a direct impact on preservation success. The disclosed method allows removal of moisture at rates which exceed what a vacuum can accomplish, which was the previously known method for moisture removal from pollen. The disclosed novel process also permits alteration of the rate of drying. For example, moisture may be removed at a rapid rate to start with, and then the relative humidity levels can be altered in order to reach the target of 15-30% pollen moisture content at a more gradual rate. Experimental data have shown that drying below 15% pollen moisture content results in much lower viability of the preserved pollen.

The present disclosure demonstrates that pollen viability can be preserved, and even enhanced, as a result of field conditioning following collection. While it was previously known that freshly-collected pollen of grass species could be stored, it has not previously been demonstrated that post-collection field conditioning of such pollen using both temperature and humidity can, on a large-scale basis, improve pollen viability and enhance storage. A large-scale basis is defined as quantities of pollen measuring about 5 grams or more, including quantities measured as kilograms of pollen. As demonstrated in Example 4, pollen under vapor pressure deficit stress collected from a range of maize inbreds showed significant improvement in percent germination after being subjected to a brief field conditioning treatment. The field conditioning treatment served to "rescue" stressed, dehydrated pollen grains thereby reversing their decline in viability and improving their capacity for germination. As disclosed in Example 4, the field conditioning of stressed pollen grains with 100% relative humidity improved germination by 21%, on average. Adding cold treatment at 4° C. produced a synergistic effect that increased germination by 33%. The field conditioning effect was detectable within one hour. Hot, dry conditions, which are typical during peak pollen shed in the field, cause pollen to lose moisture content and expire more rapidly. The combined treatment of high relative humidity and low temperature slows pollen metabolism while maintaining moisture content, thereby extending its viability.

Once the method of field conditioning pollen had been established, further experimentation was done to determine optimal conditions for the storage of the field conditioned pollen.

Pollen that has been subjected to the field conditioning process can subsequently be subjected to further preservation techniques or can be stored. If desired, the pollen can be subjected to the field conditioning step and then used in pollinations.

Pollen can be subjected to additional preservation steps in order to increase its ability to retain viability and fertility over storage periods. It is beneficial to field condition the pollen as previously described prior to such preservation techniques or storage, in order to maximize pollen health and viability prior to any storage. The preparation of pollen for storage requires a careful process including an environment with known relative humidity levels, as well as specific temperature and atmospheric pressure conditions. In addition, the presence of useful gases will assist in maximizing storage success.

It is initially necessary to remove some moisture from the pollen in order to maximize the pollen's viability and fertility, as demonstrated in Example 8, and is particularly critical prior to long-term cryogenic storage. Establishing an environment with a known relative humidity serves to gradually remove moisture from the pollen, thereby acting as a drying agent. Ideally, the relative humidity in the drying environment should be any value ranging from about 0% to about 30% relative humidity including about 0%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25% about 26%, about 27%, about 28%, about 29%, and about 30% humidity. The lower the relative humidity level threshold, the faster moisture is removed from the pollen. The moisture content of fully hydrated pollen is typically about 60%. A target moisture content of the pollen prior to cryogenic storage is a value in the range of about 15% to about 35%, including about 35%, about 34%, about 33%, about 32%, about 32%, about 30%, about 29%, about 28%, about 27%, about 26%, about 25%, about 24%, about 23%, about 22%, about 21%, about 20%, about 19%, about 18%, about 17%, about 16% and about 15% moisture content. The relative humidity can be adjusted over time to allow the rate of drying to increase or decrease. In the field, pollen which falls below 30% moisture content has lost viability completely for in vitro germination (Fonseca and Westgate (2005) *Field Crops Research* 94: 114-125). By contrast, in the present invention, pollen fertility and viability are maintained when pollen moisture content is reduced under cold conditions in an environment that achieves target pollen moisture content. The critical factor is a very controlled drying process, which cannot be achieved in the field.

The process of reducing the pollen moisture content may be conducted at different temperatures ranging from −10 to 25° C.

The addition of targeted pressure treatment to the pollen showed that pollen viability during storage with high humidity and low temperature may be improved if stored at specific pressures, which in some embodiments is below atmospheric pressures. This concept is demonstrated by Examples 5, 6, and 7. Specifically, in some embodiments of the invention, introduction of a vacuum serves to reduce and/or prevent oxidative stress on the pollen and, therefore, increase viability. Examples 5-7 below show that viability during storage with high humidity and low temperature is sometimes improved if the pollen is further stored below atmospheric pressure. As those skilled in the art will understand, the optimal pressure (negative or positive) may vary depending on the species of pollen and the genetic background of the specific pollen within a species. Moreover, in some embodiments a vacuum may be optimal, whereas in other embodiments pressures at or above atmospheric pressure may be optimal. Experimentation based on the examples provided herein below will allow for optimization of the pressure to maximize the preservation of the pollen's viability.

In maize, for example, storage at about 15 kPa-150 kPa is optimal, as shown in Example 6. Moreover, storage at reduced pressures of about 67 kPa-94 kPa may be most optimal, including pressures about 67 kPa, 68 kPa, 69 kPa, 70 kPa, 71 kPa, 72 kPa, 73 kPa, 74 kPa, 75 kPa, 76 kPa, 77 kPa, 78 kPa, 79 kPa, 80 kPa, 81 kPa, 82 kPa, 83 kPa, 84 kPa, 85 kPa, 86 kPa, 87 kPa, 88 kPa, 89 kPa, 90 kPa, 91 kPa, 92 kPa, 93 kPa, and 94 kPa. In some experiments, including Example 6 below, a reduced pressure around 84.3 kPa may provide for pollen viability which is nearly doubled compared to storage at atmospheric pressure. Accordingly, storage in reduced pressure, combined with increased humidity and low temperature improves pollen viability. Moreover, storage under reduced pressure may maintain increased viability for all periods of preservation and storage and allow pollen to be held for extended periods for later use. Of course, the optimal pressure conditions and improvements to viability may differ across plant species and within each species across genetic backgrounds.

Furthermore, in some embodiments of the invention, adjustment of the initial PMC may provide advantages, as demonstrated below in Example 8. In some embodiments, dehydration of the pollen prior to storage improves viability of the stored pollen. Typical fresh pollen moisture content is about 60%. Moreover, dehydration of the pollen during a field conditioning step combined with a specific relative humidity level during storage may provide optimal pollen storage conditions to prevent and/or reduce loss of viability. The equilibrium moisture content of the stored pollen may be optimized to maintain and/or slow loss of viability. In some maize examples, equilibrium moisture content of about 45%, about 46%, about 47%, about 48%, about 49%, about 50%, about 51%, about 52%, about 53%, about 54%, about 55%, about 56%, about 57%, and/or about 58% may maintain and/or slow loss of viability. Moreover, striving for an optimized equilibrium moisture content has shown to provide better results than simply storing pollen in a high humidity environment.

The addition of gases, such as nitrogen ($N_2$) or carbon dioxide ($CO_2$), serve several functions in preparing the pollen for storage, as shown in Examples 10, 11, and 12 below. The first function is that the gases can serve as drying agents. The moisture content of these gases is typically below 1.0%. Constantly flowing a refreshed source of gas to the chamber where the pollen is being retained ensures that the moisture liberated from the pollen is exhausted from the system. The gases also serve to displace oxygen from the chamber. Oxygen is required by the pollen for metabolic activity, and promotes accumulation of reactive oxygen species (ROS). Reducing metabolic activity helps field condition the pollen and prepare it for storage.

The chamber containing the pollen intended for storage is subjected to a positive pressure, or a flow of treated air to the chamber. This pressure may be established through the pumping of treated air into the chamber as demonstrated in Examples 10, 11, and 12. The positive pressure of the treated air flow may extract, add, or maintain pollen moisture and further may extract, add, or maintain chamber moisture, allowing for the careful control of the relative humidity (RH) level. The RH and temperature of the air can be established using any combination of desiccants, salt solutions, heat, or other treatments to maximize its effectiveness in controlling drying of the pollen.

During the phase of drying the pollen to 15 to 35% moisture content, the air in the chamber containing the pollen is maintained from about −10° C. to about 10° C., including about −10° C., about −9° C., about −8° C., about −7° C., about −6° C., about −5° C., about −4° C., about −3° C., about −2° C., about −1° C., about 0° C., about 1° C., about 2° C., about 3° C., about 4° C., about 5° C., about 6° C., about 7° C., about 8° C., about 9° C. and about 10° C. This can be achieved by placing the chamber in a chilled room or by introducing chilled air into the chamber through a variety of means.

Optionally, during the period of pollen drying, the pollen contained within the chamber may be agitated mechanically. The agitation serves to expose the maximum surface area of the pollen to the air in the chamber, thereby providing for more even drying and preventing clumping of the pollen. This may be achieved in a number of different ways, including the use of vibration, forced air, rotation, or other means.

Once the pollen has reached the optimal moisture content of 15 to 35% moisture, it can be stored. Storage can be achieved by placing the chamber of pollen in liquid nitrogen, in freezing conditions of −80° C. to 0° C., in refrigeration, or at atmospheric conditions. The choice of conditions in which to store the pollen may depend upon the timeframe in which the pollen is expected to be used.

As explained in detail in the preceding paragraphs, maximizing and extending the viability of pollen using the disclosed method requires careful manipulation of a number of factors within defined ranges. Laboratory-generated data using maize pollen as a test species have indicated the conditions for improving pollen viability include modification of one or more conditions within the chamber to fall within the disclosed ranges as set forth below.

The relative humidity of the chamber containing the pollen may be maintained at any value ranging from about 75% humidity to about 100% humidity, including about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, and about 100% humidity The temperature of the chamber containing the pollen may be maintained from about −10° C. to about 10° C., including about −10° C., about −9° C., about −8° C., about −7° C., about −6° C., about −5° C., about −4° C., about −3° C., about −2° C., about −1° C., about 0° C., about 1° C., about 2° C., about 3° C., about 4° C., about 5° C., about 6° C., about 7° C., about 8° C., about 9° C. and about 10° C.

The concentration of oxygen ($O_2$ gas) present in the chamber may be moderated from about the prevailing atmospheric percentage to about 0%, including about 21%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, and about 0% oxygen.

The concentration of nitrogen ($N_2$ gas) present in the chamber may be moderated from about atmospheric percentage to about 100%, including about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, and about 100% nitrogen.

Furthermore, the atmospheric pressure and carbon dioxide ($CO_2$ gas) concentration within the chamber may be modified to improve viability as outlined below. The atmospheric pressure inside the chamber may be modified in a manner that supports the tight control of humidity levels. Furthermore, the modification of air pressure allows for the prevention of oxidation of the pollen. Appropriate atmospheric pressures range from about 15 kPa to about 150 kPa, including about 15 kPa, about 20 kPa, about 25 kPa, about 30 kPa, about 35 kPa, about 40 kPa, about 45 kPa, about 50 kPa, about 55 kPa, about 60 kPa, about 65 kPa, about 70 kPa, about 75 kPa, about 80 kPa, about 85 kPa, about 90 kPa, about 95 kPa, about 100 kPa, about 105 kPa, about 110 kPa, about 115 kPa, about 120 kPa, about 125 kPa, about 130 kPa, about 135 kPa, about 140 kPa, about 145 kPa, or about 150 kPa.

The concentration of $CO_2$ present in the chamber may be moderated from about atmospheric percentage (about 0.04%) to about 100%, including about 1%, about 10%, about 20%, about 30%, about 40%, about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, and about 100% $CO_2$.

Following the modification of the conditions inside the chamber, the pollen is maintained in the defined conditions for a period of time to allow the improvements in pollen viability to take place, and as a result, extending the viability of the pollen. Even such field conditioning for a short period of time, including but not limited to 60 minutes, can improve the viability of the pollen and extend the duration of the viability window. Initial laboratory results have shown the overall viability of maize pollen improved significantly, more than four-fold for many genetic backgrounds, after 24 hours in the field conditioning environment (see Example 3). In addition, the window of viability of maize pollen has been extended with this field conditioning method. Laboratory results have shown that maize pollen, which normally has a viability window of approximately less than 2 hours, has a viability window extended to approximately 17 days, following treatment with the method of the invention (Example 8).

Accordingly, in one optimal embodiment, pollen may be collected from actively shedding plants and placed into a preservation chamber. The preservation chamber may include a constant flow of nitrogen gas. The preservation chamber is adjusted for a target pollen moisture content, such as about 30%. As the pollen moisture content decreases, the temperature in the chamber can slowly be adjusted downward, also, such as to about −5° C. Preferably the temperature adjustment occurs without freezing the pollen. Similarly, the relative humidity levels in the chamber can also be adjusted to increase or decrease the rate of pollen dehydration. The relative humidity in the chamber may eventually be increased if necessary to stabilize the final pollen moisture content at about 30%. Optimally, this process is accomplished in approximately 100 minutes, although other time periods may be used without departing from the scope of the invention and with success.

Pollen subjected to such a method may be used in any application where pollen is a commercial or experimental unit. In one example, the field conditioned and preserved pollen may be used to produce seed, hybrid, parent, or otherwise, in any setting, including but not limited to a laboratory, greenhouse, and field. In another example, the field conditioned and preserved pollen may be used to produce grain, hybrid or otherwise, in any setting, including but not limited to a laboratory, greenhouse, and field. Moreover, as discussed above, such a method may be applied to pollen from the Poaeceae (Gramineae) family of plants, as well as any other plant species wherein it is desired to field condition and preserve pollen.

The field conditioning and preservation techniques disclosed in this invention are intended to successfully treat and preserve pollen such that the field-conditioned and/or preserved pollen maintains its viability to the extent that about 4 to about 20 grains of pollen are sufficient to successfully pollinate an embryo.

As noted above, although the invention has applicability to maize and the maize industry, the invention is applicable to storage and preservation of all types of pollen. In another example, rice pollen may be successfully preserved, as provided in Example 9 below. Specifically, in the provided Example, rice pollen was preserved at 4° C. and 100% relative humidity for 20 hours. The preserved pollen showed a germination rate of 25%, proving that the methods of the present invention are applicable to other plant species. Moreover, using the experimental methods described herein, one skilled in the art may optimize the present invention for a desired species of pollen. The following examples illustrate the present invention in more detail and are illustrative of how the invention described herein could be implemented in maize.

Example 1: Effect of Genotype on Pollen Health

A study was undertaken to determine the effect of plant genetic background on the viability and overall health of freshly-shed pollen. Fresh pollen was collected from field grown maize plants of eight genetic backgrounds in Grimes, Iowa at approximately 11:30 am on Aug. 14, 2016. The genetic backgrounds were selected to represent a broad sample of heterotic groups known in maize breeding. Tassels of the plants were vigorously brushed free of adhering anthers and pollen at 9:00 am the same day. Pollen from tassels of approximately 10 plants of each genetic background was collected into a separate paper bag. Pollen was separated from debris by passage through a screen (150 micron pore size) and immediately placed into field conditioning at 4° C. for 80 minutes. Field conditioning involved spreading a thin layer of pollen in the bottom of a 15 cm petri plate that had prechilled water-moistened blotter paper held in the upper half of the plate. Following field conditioning, pollen within each plate was gently mixed to obtain homogeneity and a small portion assayed for viability. In vitro germination was used to assess viability by incubating pollen in an artificial media (438 mM sucrose, 1.6 mM $H_3BO_3$, 3.0 mM $CaCl_2$—$H_2O$) for one hour at 22° C. Duplicate assays were conducted. With the aid of a microscope, percent germination was measured as the number of pollen grains with a pollen tube length more than twice the diameter of the grain from a random sample of typically 200 grains.

Many factors can affect the viability of pollen, including genetic background. As demonstrated in Table 1, the viability of pollen among eight diverse genetic backgrounds of maize differed significantly by approximately two-fold when sampled on a single day. Genetic lines of maize are reported to show large differences in the tolerance of pollen to stress, particularly heat stress and vapor pressure deficits that lead to dehydration. For these reasons, when assessing methods for preservation of pollen, it is important to segregate variation in viability due to genetic differences from that which can be caused by other factors, such as handling procedures and storage conditions. Equally important, it is prudent to evaluate more than a single genetic background when determining best practices for storing pollen.

TABLE 1

Difference in viability of pollen among eight diverse genetic backgrounds of maize

| Genetic Background | In Vitro Percent Germination (Mean +/− SE) |
| --- | --- |
| AATH3 | 54 (+/−1) |
| 207 | 56 (+/−0) |
| H99 | 28 (+/−0) |
| CM105 | 63 (+/−7) |
| C103 | 45 (+/−8) |
| OQ101 | 63 (+/−9) |
| LH162 | 50 (+/−0) |
| OH43 | 39 (+/−4) |

Example 2: Effect of Laboratory Conditions on Pollen Health

A study was undertaken to determine the effect of ambient laboratory conditions on the viability of freshly-shed pollen. Fresh pollen was collected from tassels of plants grown in the greenhouse and exposed to ambient environmental conditions in the laboratory. Pollen was taken from two unrelated genetic backgrounds of maize, Yukon Chief and Silver Choice, to preclude drawing conclusions based on a sole genetic material. Immediately after collection, pollen was separated from debris by passage through a screen (150 micron pore size) and placed in a thin layer on a paper sheet set on the laboratory bench. The pollen was left in this condition without any special precautions to control the laboratory ambient temperature and relative humidity, which were 21-23° C. and 30-34%, respectively, over the course of the experiment. The pollen was mixed to obtain homogeneity and sampled for measurement of viability at 0, 1, 2, 3 and 23 hours after the start of the experiment. In vitro measured as described in Example 1, using a random sample of about 100 grains per measurement. Results are presented in FIG. 1.

The percent germination of Yukon Chief declined rapidly with exposure to laboratory ambient conditions, beginning at 88% and declining to 4% within three hours. After 23 hours of exposure only a trace of germination could be detected among grains in the pollen. Pollen of Silver Choice followed a similar pattern except the time zero value was lower than the viability at one hour exposure. The time zero value is believed to be an outlier.

The environmental conditions of the laboratory were very unfavorable for maintenance of viability in pollen of the two genetic backgrounds examined. The occurrence of high temperature stress in maize pollen is normally known to occur at temperatures in excess of 35° C. and, since the laboratory was 21-23° C., it is most likely that viability was lost quickly from these samples because the ambient relative humidity rapidly dehydrated the pollen over a three-hour period. Dehydration is known to affect the viability, and sometimes, fertility, of maize pollen.

Example 3: Pollen Field Conditioning: Cold and High Relative Humidity

A study was undertaken to determine whether the viability of field-shed pollen could be improved to reverse the negative effects of dehydration caused by vapor pressure deficit stress. Fresh pollen was collected from field grown maize plants of eight genetic backgrounds in Grimes, Iowa at approximately 1:45 pm on Aug. 10, 2016. The ambient temperature and relative humidity were 31.7° C. and 72%, respectively, during collection. The genetic backgrounds were selected to represent diverse heterotic groups known in maize breeding, and included hybrid and inbred lines. The time of collection, mid-afternoon, was chosen intentionally because the vapor pressure deficit is typically more unfavorable to pollen health when temperatures are elevated and relative humidity reduced, compared to times earlier in the day. Tassels of the plants were vigorously brushed free of loosely held anthers and pollen at 9:00 am the same day and each subsequently covered with a paper bag. At least six plants of each genetic background were bagged. Upon collection, tassels were shaken in the bags and material retrieved from the bags of each genotype passed through a screen (150 micron pore size) to collect the pollen. Each genetic pool of pollen was mixed thoroughly to obtain homogeneity. Assays for in vitro germination were immediately initiated in the field by sampling the pollen collected for each background (assay described in Example 1). In addition, each pool was sampled to measure pollen moisture content (PMC), which was calculated after weighing 50-100 mg pollen before and after drying at 104° C. for 24 hours. Promptly, the pools of pollen were subjected to field conditioning, held there for 120 minutes, and assayed again for in vitro germination, as described in Example 1. A single assay was conducted for each genetic background at each time and approximately 335 pollen grains were examined for each test.

Figure 2:
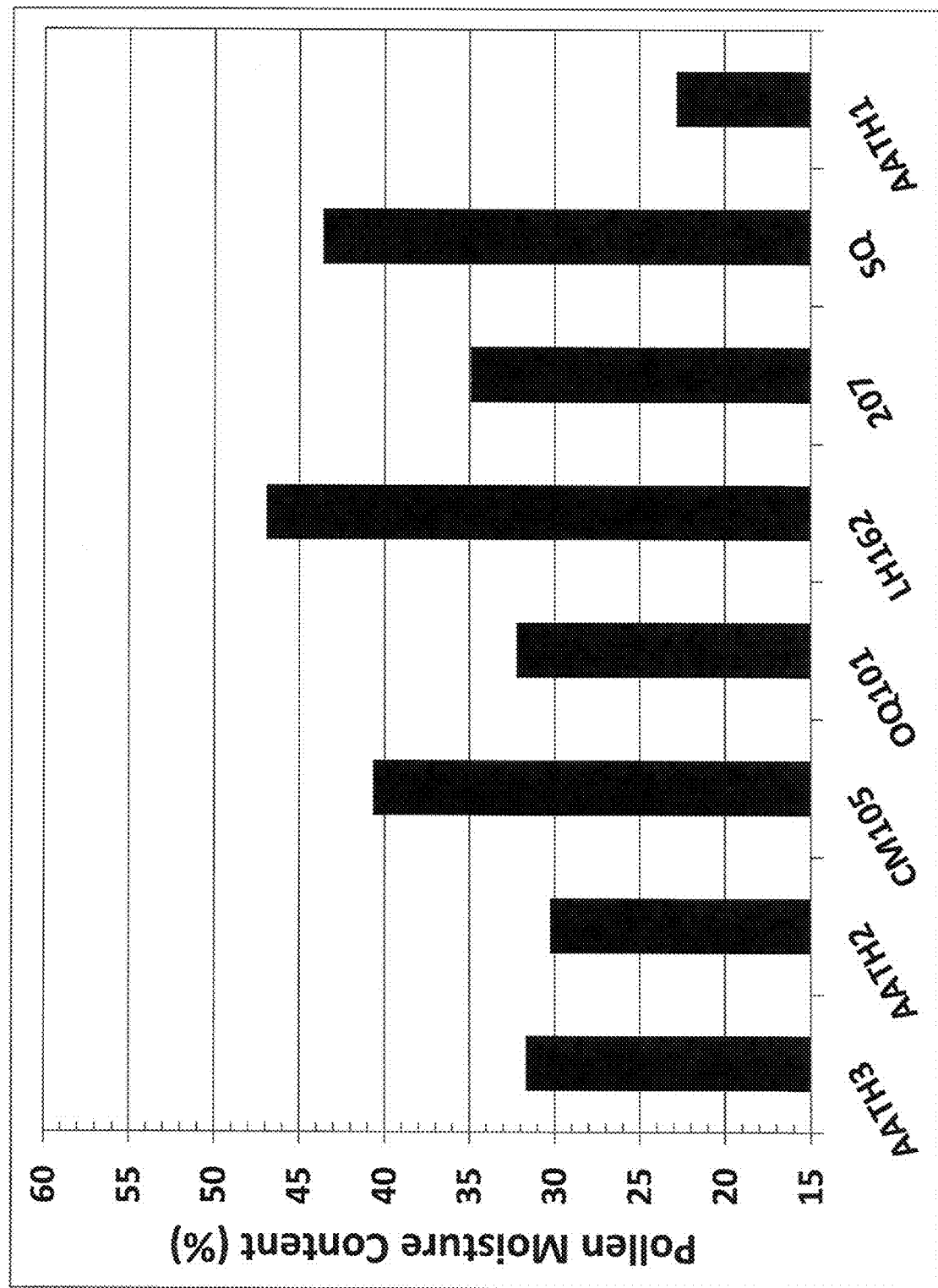
FIG. 2: This figure demonstrates the variability in the pollen moisture content of freshly-collected pollen from the field.

Fresh maize pollen typically has a PMC of roughly 60%, but in this experiment PMC values of freshly collected pollen ranged from 22.8-46.9%, with an average of 35.4% (FIG. 2). The ambient conditions at the time of pollen collection, 31.7° C. and 72% relative humidity, resulted in a vapor pressure deficit that caused the pollen that was loosely bound in the tassels to dehydrate. Genetic differences in PMC of freshly collected pollen were apparent, as similarly reported by other researchers.

Figure 3:
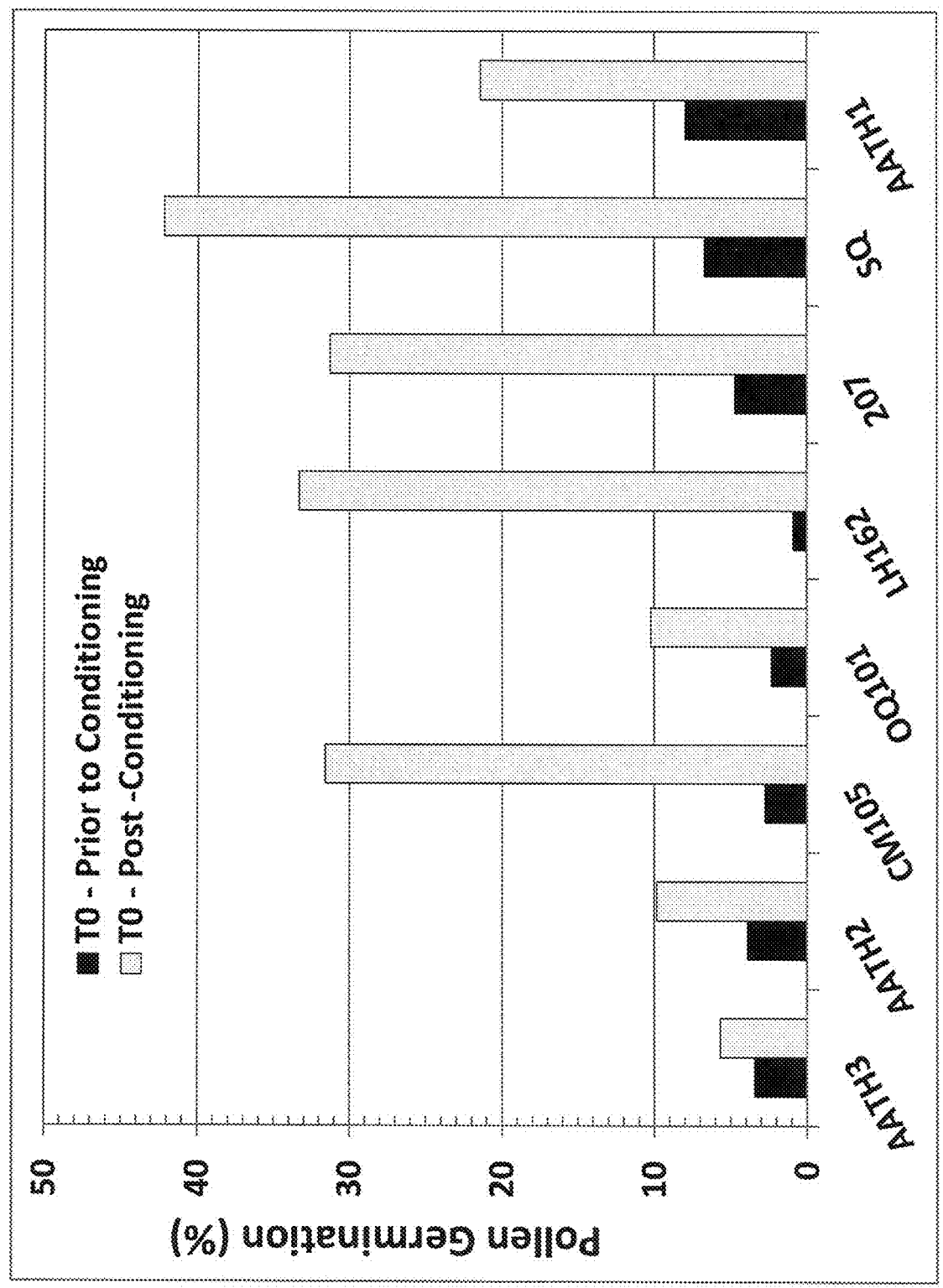
FIG. 3: This figure shows the effect of field conditioning pollen by comparing the in vitro germination rates of pollen immediately after collection and again two hours later following a period of field conditioning.

Pollen from each genetic background was tested for in vitro germination immediately after collection and again two hours later following field conditioning at approximately 4° C. and 100% relative humidity. FIG. 3 shows that at time-0, prior to field conditioning, pollen germination was less than 10% for all genotypes but pollen viability was increased, more than four-fold for many genetic backgrounds, following two hours of incubation at high humidity and low temperature. Viability of the dehydrated pollen was revived more for some genetic backgrounds than others but, as a rule, field conditioning the stressed pollen improved its ability to germinate and form pollen tubes that are required in order for pollen to fertilize ovules and form seed. Reversing the negative effects of stress and dehydration on pollen viability and fertility through field conditioning can play an important role in storing pollen in preparation for its use as a pollination supplement to improve the purity and yield of seed produced in seed and grain production.

Example 4: Pollen Field Conditioning: Effect of Temperature Versus Relative Humidity A study was undertaken to determine whether the chilling or the high relative humidity produced the rescue effect noted in Example 3, and to determine how quickly this effect occurred. Fresh pollen was collected from field grown maize plants of four genetic backgrounds (Mo17, C103, AATH1, AATH3) in Slater, Iowa on Jul. 27, 2016. The genetic backgrounds were selected to represent diverse maize germplasm, and included hybrid and inbred lines. Tassels were vigorously brushed free of loosely held pollen, bagged, and pollen collected as described in Example 3. Assays for in vitro germination were immediately initiated in the field and pollen sampled for PMC as also described in Example 3. Promptly upon collection, the pools of pollen were placed into field conditioning, using thin layers of pollen in hydrated 6 cm petri plates, as described in Example 1. The samples were field conditioned, at the field location, at either 4° C. or 22° C. for two hours. Pollen was sampled every hour for in vitro germination, as detailed in Example 1. A single assay was conducted for each genetic background at each time point and approximately 206 pollen grains were examined for each test.

Pollen field conditioning was performed with a single, high level of relative humidity (ca. 100%) and two incubation temperatures. A factorial treatment scheme with level of relative humidity for field conditioning was not possible at the test location. Hence, the experiment examined how field conditioning with high humidity influenced pollen viability compared to its initial level (i.e., time of pollen collection) and whether the combination of high humidity with low temperature provided any unique benefit.

Figure 4:
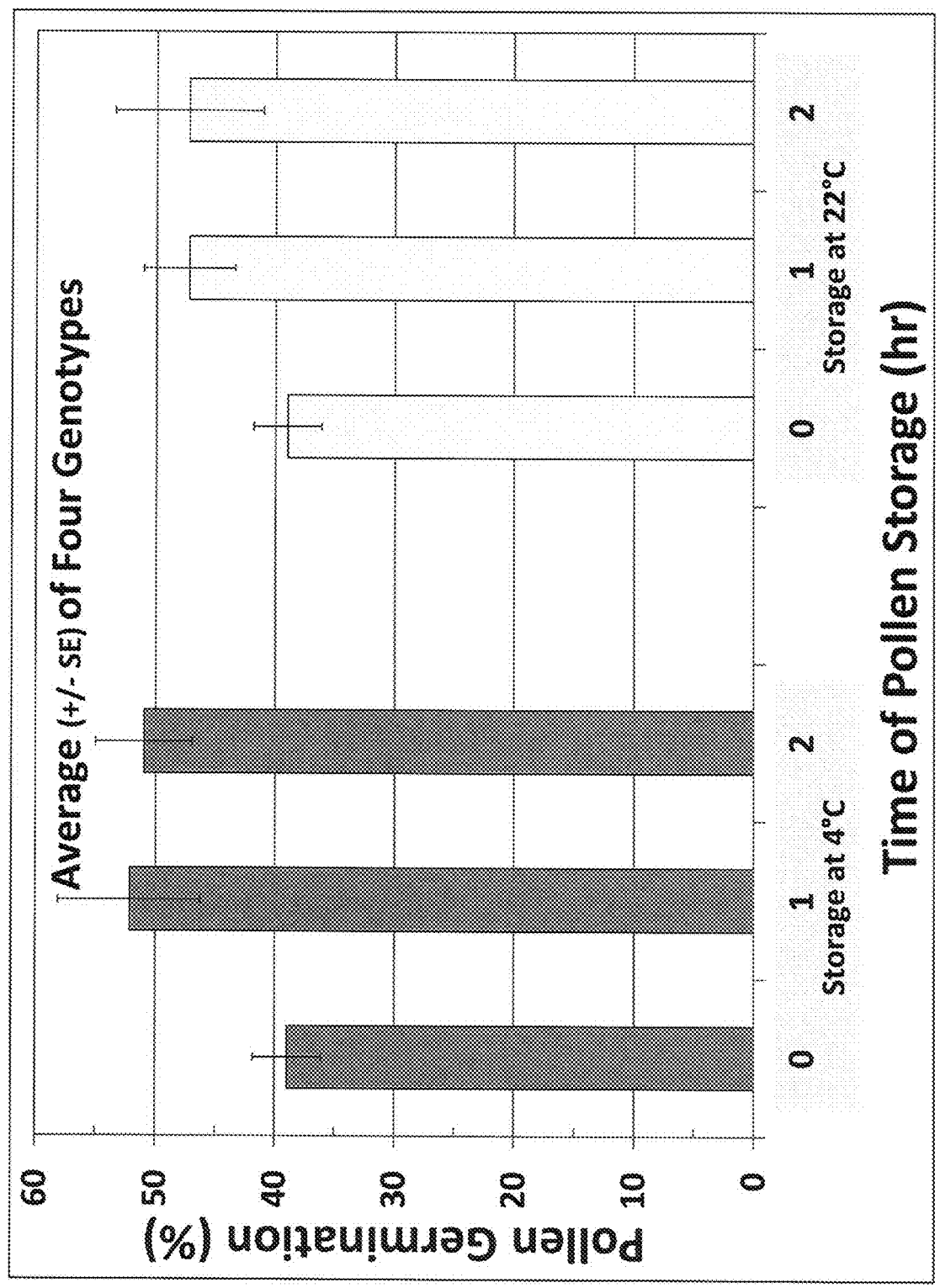
FIG. 4: This figure demonstrates the average pollen germination percentages of four maize genotypes following storage of the pollen in high humidity conditions for one hour at either 4° C. or 22° C.

The PMC of pollen at time of collection ranged from 51.9% to 59.2%, so none of the inbreds or hybrids demonstrated severe dehydration or stress of the pollen. Average viability of the four genetic backgrounds across treatments is shown in FIG. 4. Pollen hydration was good, to excellent, at the start of field conditioning but viability was slightly low, as indicated by pollen average in vitro germination rates of 39%. After 60 minutes or less, at "normal" temperature (22° C.), hydration of fresh pollen increased germination by 21%, on average. Hydration plus cold treatment (4° C.) increased germination 33%, on average. In summary, field conditioning the pollen elevated low viability samples within one hour, primarily due to the presence of high humidity, but additional benefit was gained from storage at low temperature.

Figure 5:
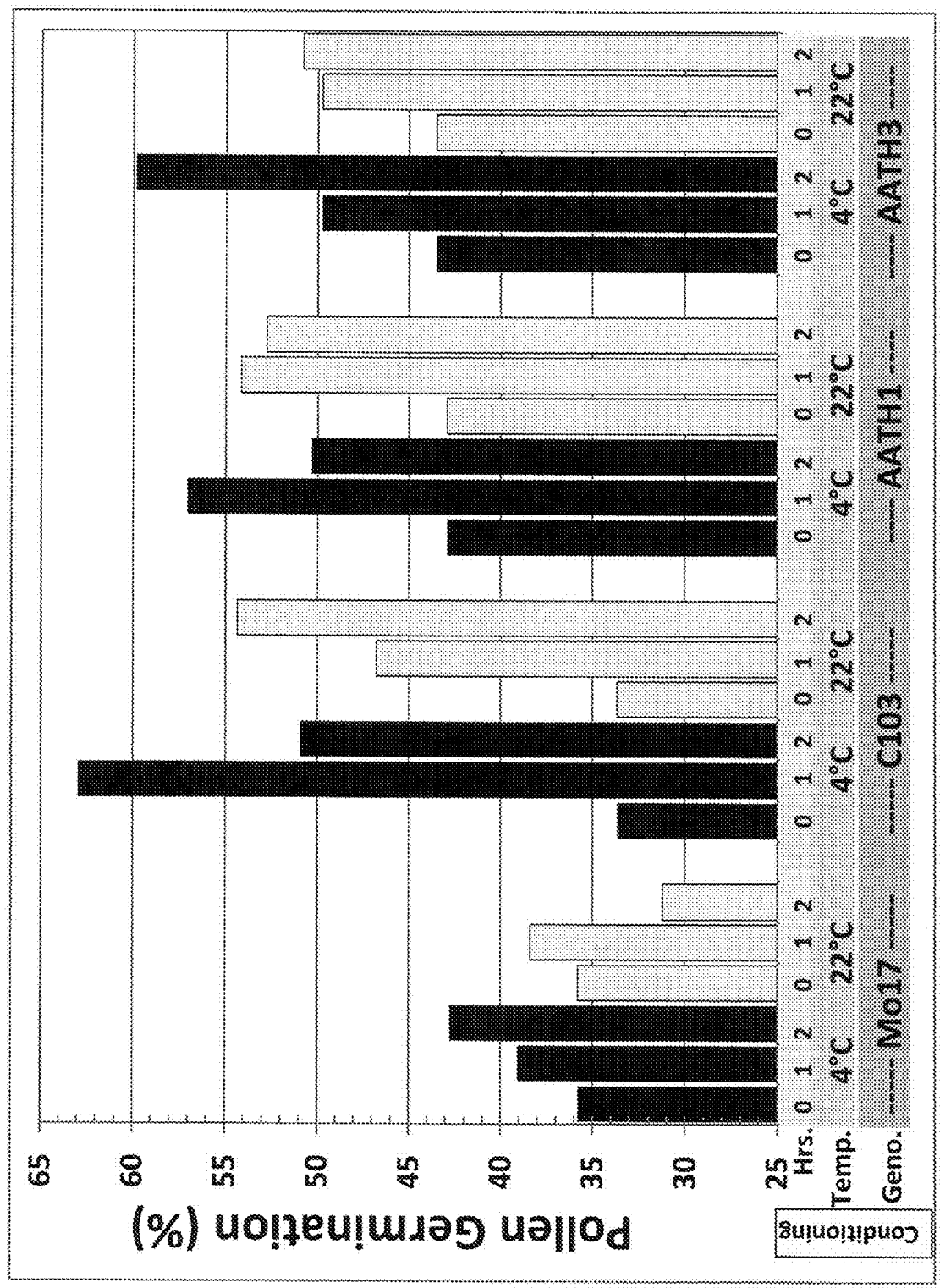
FIG. 5: This figure shows the effect of field conditioning on revitalization of pollen viability across multiple genotypes. For each genotype, the effects of revitalization in response to high humidity and the advantage obtained by field conditioning at low temperature are shown.

Details of the effect of field conditioning on revitalization of pollen viability is shown for each genetic background in FIG. 5. The importance of examining multiple genotypes in order to gain a clearer picture of how field conditioning and storage processes affect maize, in general, are again evident. Genotypic differences occurred for, (a) viability at time of pollen collection (e.g., C103 vs. AATH1), (b) revitalization response to high humidity (e.g., Mo17 vs. C103) and (c) advantage obtained by field conditioning at low temperature (e.g., Mo17 vs. C103). Despite genetic differences, it was nearly always true that the viability of fresh pollen can be improved by short term storage at high humidity and low temperature.

Example 5: Pollen Field Conditioning: Vacuum Treatment

Experiments conducted had shown an ability to collect pollen under environmentally stressful conditions and to improve its viability by field conditioning it under specific temperature and relative humidity conditions. It was theorized that oxidative stress could be responsible for deterioration of germinability when pollen is stored over a period of days. Experiments were conducted to remove oxygen from the storage environment to determine whether this improved the duration of viable pollen storage. Anoxic conditions were obtained by vacuum evacuation.

Fresh pollen was collected from field grown maize plants of nine genetic backgrounds (B14, C103, SQ, B37, 207, LH162, AATH1, AATH3) between 9:45 am and 1:10 pm in Slater, Iowa on Jul. 22, 2016. The genetic backgrounds were selected to represent diverse heterotic groups known in maize breeding, and included hybrid and inbred lines. Pollen of hybrid AATH1 was sampled from plants grown in two different areas of the field. Tassels were vigorously brushed free of loosely held pollen and bagged the evening before the day of use. Pollen was collected as described in Example 3.

Each genetically unique pool of pollen was sampled for PMC immediately after collection. PMC was measured as described in Example 3. Each pool of pollen was then split into halves and promptly placed as a thin layer in the lower half of a 6 cm petri plate. Each plate was loosely covered with a paper fiber wipe (Kimwipe). As collected, covered petri plates were placed on a rack held in a 3.78 L stainless steel vacuum chamber. In the bottom of each chamber was 200 mL of prechilled water. Each tank was covered with an acrylic lid tightly secured by rubber bands or vacuum. One half of each pollen sample was placed in a chamber with atmospheric pressure (101.3 kPa) or a vacuum (50.5 kPa pressure). The chambers were surrounded by ice in coolers while samples were collected in the field and then transferred to a 5° C. incubator in the laboratory. After six days of storage, chambers were opened, pollen samples mixed to homogeneity, sampled for PMC, and pollen assayed for in vitro germination as described in Example 1. A single assay was conducted for each genetic background and an average 298 pollen grains were examined for each test.

Figure 6:
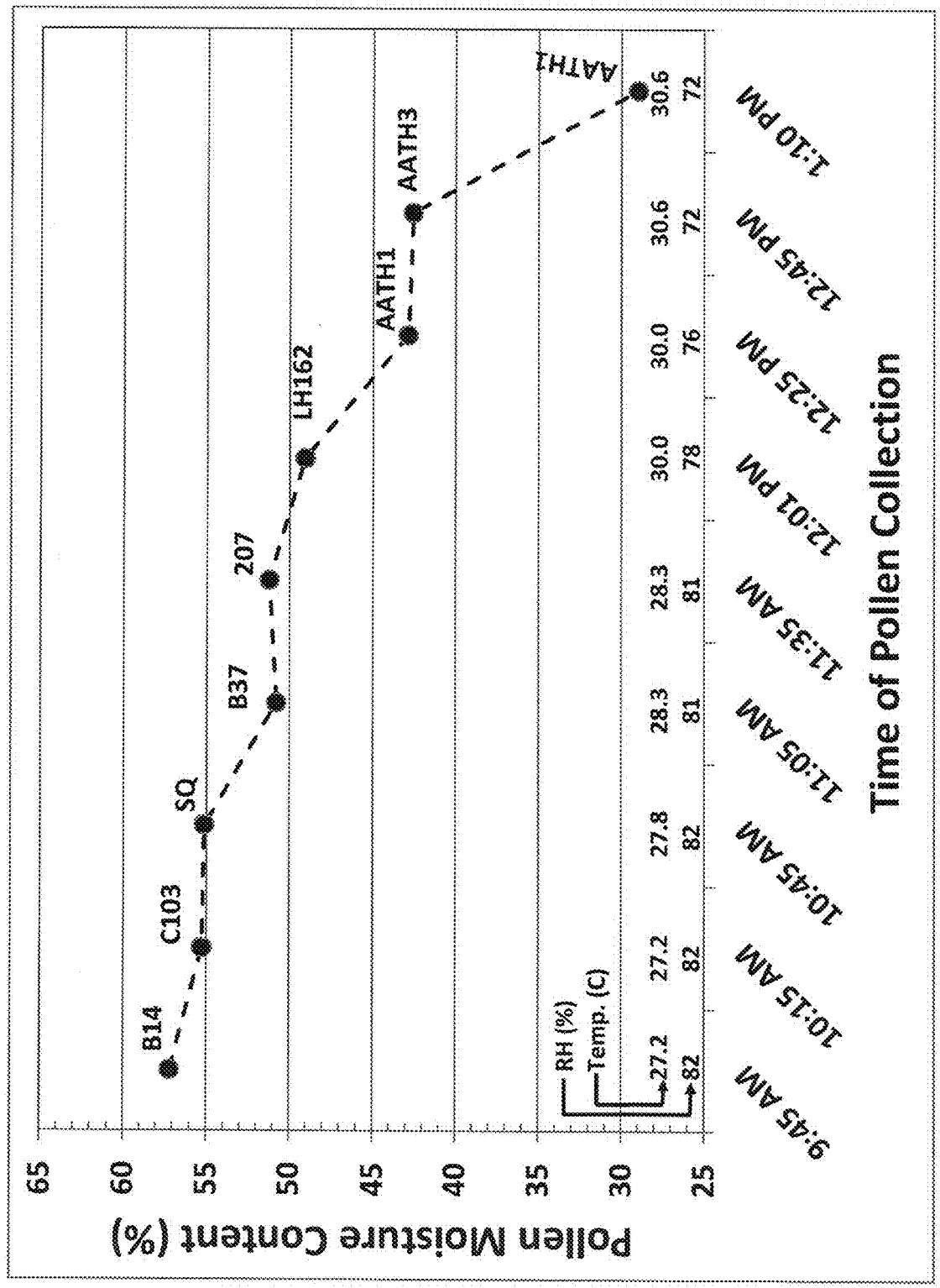
FIG. 6: This figure shows the change in pollen moisture content in different genotypes based on the time of day that the pollen collection took place.
Figure 7:
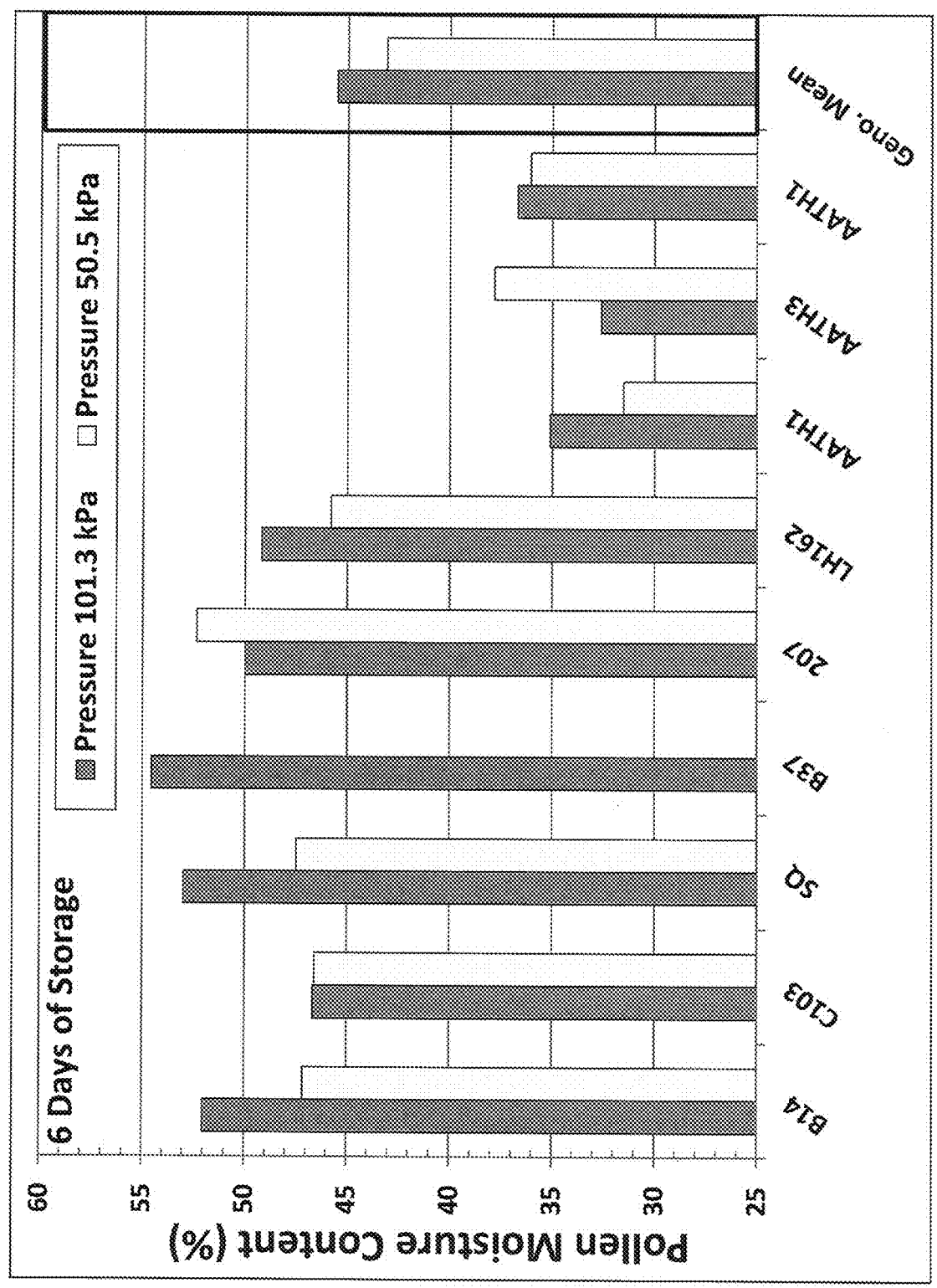
FIG. 7: This figure demonstrates the effect on pollen moisture content of storing freshly-collected pollen for 6 days at two different pressure levels while maintaining a high humidity level.
Figure 8:
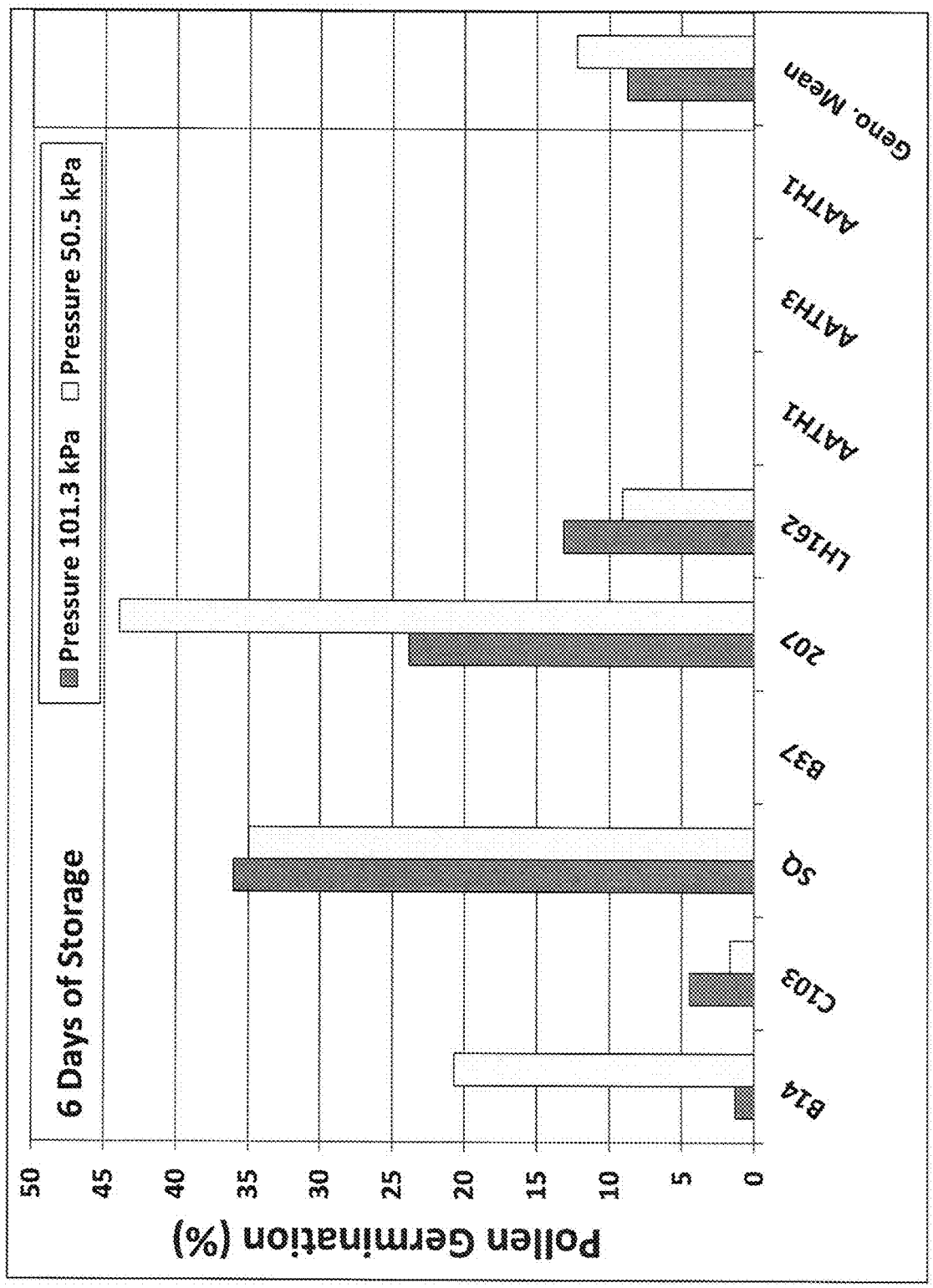
FIG. 8: This figure shows the change in pollen germination percentage following the storage of freshly-collected pollen for 6 days at two different pressure levels, both at a high humidity level.

Pollen became more dehydrated as collection occurred later in the day (FIG. 6). This response has been observed often in our experiments and by others (Kaefer, K. A. C., et al. (2016) *Afr J Agr Res*, 11(12), pp. 1040-104). When stored for six days at high humidity, most samples failed to hydrate to a great degree, especially those severely dehydrated at time-0 (compare FIGS. 6 and 7). Therefore, pollen of some genetic backgrounds (e.g., B37, AATH1, AATH3) was stressed before and during storage and failed to germinate, regardless of storage pressure. For other backgrounds, the PMC ranged from 45-55% following storage and pollen remained viable for six days (FIGS. 7, 8). Storage at the lower pressure caused pollen, on average, to become slightly drier. There were wide differences in the effect of pressure on PMC depending upon the genetic background and initial PMC. Among samples viable after six days storage, pollen germination was slightly greater when stored at reduced pressure and oxygen level (FIG. 8). Again, treatment effect differed across genetic backgrounds but the data suggested that viability during storage with high humidity and low temperature is generally improved if stored below atmospheric pressure.

Example 6: Pollen Field Conditioning: Vacuum Titration

Given the recognized advantage of storing pollen under vacuum, experiments were designed to titrate the level of vacuum necessary for maximizing the preservation of the pollen's viability.

Fresh pollen was collected from field grown maize plants of six genetic backgrounds (OH43, Mo17, C103, H99, LH162, OQ101) between 10:30 am and 1:10 pm in Slater, Iowa on Jul. 20, 2016. The backgrounds represented maize inbreds of diverse heterotic groups. Tassels were vigorously brushed free of loosely held pollen and bagged the evening before the day of use. Pollen was collected and immediately (i.e., Time-0) sampled for determination of PMC and in vitro germination, as described in Example 3. Each genetic pool of pollen was then split into six equally-sized fractions. Each fraction was placed as a thin layer in the bottom of a 6 cm petri plate that was subsequently covered with a paper fiber wipe. One plate of each genetic background was set on a rack that was placed into one of seven 3.78 L stainless steel vacuum chambers. In the bottom of each chamber was 200 mL of prechilled water. Each chamber was covered with an acrylic lid and held at ambient pressure (101.3 kPa) and 5° C. for 24 hours. After one day of field conditioning, one of the chambers were briefly opened and pollen subsampled again for in vitro germination assay. Air was then evacuated from the chambers to 84.3, 67.4, 50.5, 33.5, 16.6, or 8.5 kPa pressure. One chamber remained at 101.3 kPa. All chambers were then incubated at 5° C. for six days before a final measurement of PMC and in vitro germination. A single germination assay was conducted for each genetic background at each time and approximately 285 pollen grains were examined for each test.

Figure 9:
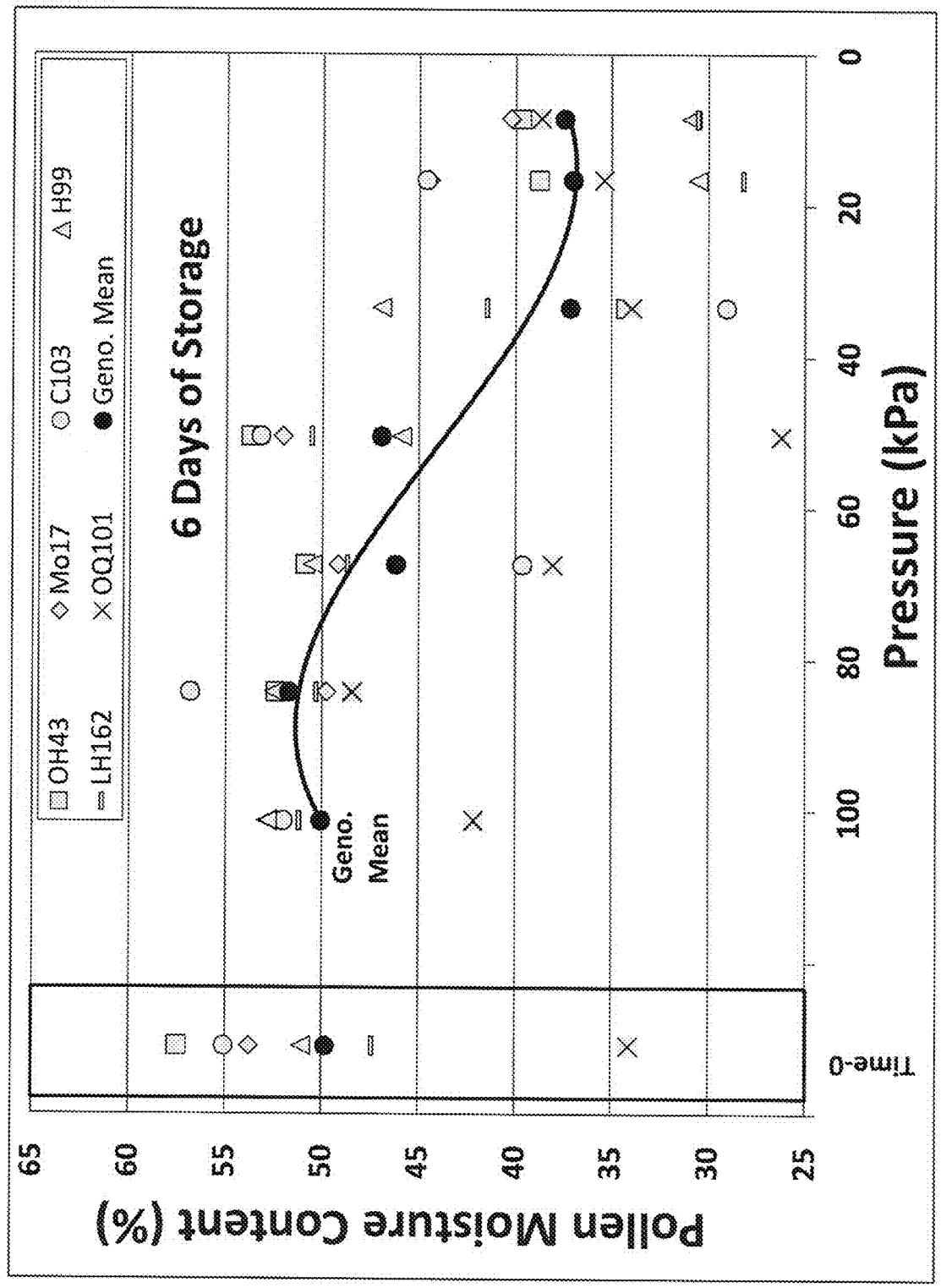
FIG. 9: This figure shows the change in pollen moisture content across six different genetic backgrounds at time zero, and after six days of storage at different air pressure values.
Figure 10:
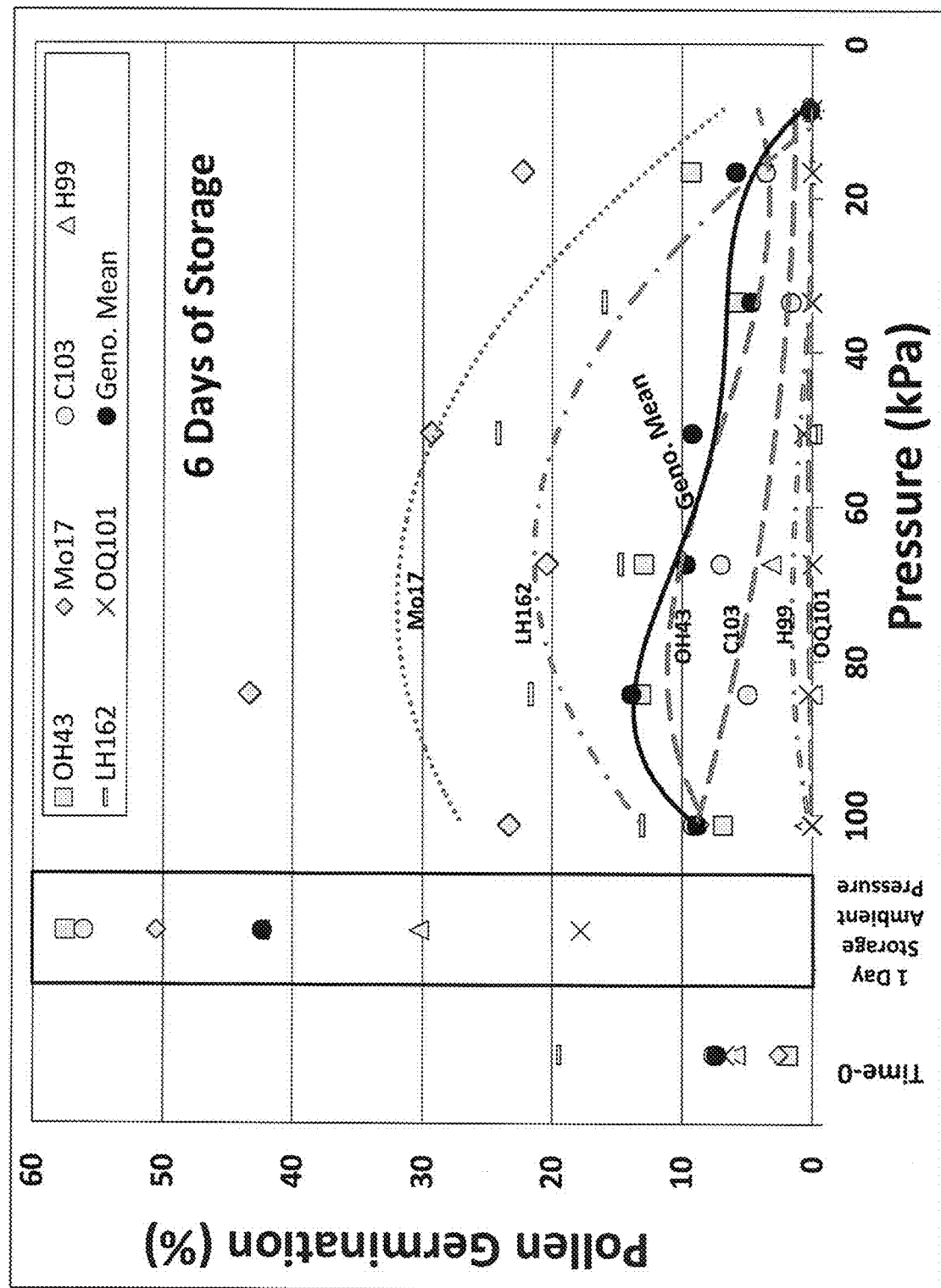
FIG. 10: This figure shows the variation in pollen germination percentages across six different genetic backgrounds at time zero, after 1 day of field conditioning at ambient air pressure, and after six days of storage at different air pressure values.

At Time-0, when pollen was initially collected in the field, most pollen samples were fairly well hydrated, as indicated by an average PCM of 49.8% (FIG. 9). Only pollen of inbred OQ101 was dehydrated, with a PMC of 34.1%. Despite these levels of hydration, viability of all pollen backgrounds was poor and average in vitro germination was only 7.4% (FIG. 10). One day later, after field conditioning in a high humidity, low temperature environment, viability was greatly improved and in vitro germination averaged 42.4%. This response was very similar to that described in Example 3 (FIG. 3). Following revitalization provided by 24 hours of field conditioning, the samples were ready to be further incubated at high humidity and low temperature, but now under reduced levels of pressure and oxygen.

Storage for six days at high humidity and low temperature did not change the average PMC of pollen maintained at atmospheric pressure (101.3 kPa) or 84.3 kPa, But as storage pressure and oxygen level declined further with increasing vacuum, pollen became more dehydrated. Average PMC following six days of storage declined from 50.1% at atmospheric pressure to 37.1% at pressures of 33.5 kPa, or lower. Patterns among the genetic backgrounds were all similar, in that PMC declined as storage pressure declined.

Two inbreds, H99 and OQ101, did not maintain viability under any vacuum treatment after six days of storage (FIG. 10). Inbred C103 tended to decline in viability as pressure and oxygen were reduced, very similar to that observed for C103 in Example 5 (FIG. 8). The other three inbreds tested in this example displayed a pattern where viability during storage was improved if pollen was stored under a slight vacuum with pressures of 67-84 kPa (FIG. 10). On average, the best level of vacuum for storage was 84.3 kPa, where viability was nearly doubled compared to storage at atmospheric pressure. Genotypes differed in how well storage under a slightly reduced pressure improved longevity of the pollen but, as a rule, maize pollen can maintain its viability better if stored under a slight vacuum with high humidity and low temperature. This is the first report to demonstrate the advantage of, and optimization for, preserving Gramineae pollen viability at reduced pressure and/or reduced oxygen.

Example 7: Pollen Field Conditioning: Vacuum Time Course Study

Experiments were designed to improve understanding of the dynamics of vacuum-enhanced storage by developing a time course study to examine the effect of timing on the preservation of the pollen's viability.

Pollen was collected from field grown plants of eight genetically diverse maize backgrounds, as before (Example 1). After the pollen was field conditioned with high humidity and low temperature for 80 minutes, the rate of in vitro germination and PMC were measured (refer to Examples 1 and 3 for method of measurement). Each pool of pollen was then divided into two, and each half was spread as a thin layer in a 6 cm petri plate covered with a paper fiber wipe. The plates were placed on a rack in one of two 3.78 L stainless steel vacuum chambers. With pollen of each genotype occurring in each chamber, acrylic lids were securely attached. One chamber remained at atmospheric pressure (101.3 kPa) and from the other, air was withdrawn to establish a pressure of 67.4 kPa. The chambers were incubated at 5° C. and very briefly opened after 3, 5, and 8 days of storage to again sample pollen pools for in vitro germination. Measurements of in vitro germination were conducted in duplicate on Day-0 of storage but as single assays at all other times. An average of 254 pollen grains were examined for each in vitro germination assay.

After collecting pollen from tassels and field conditioning it for 80 minutes, the PMC ranged from 50.0 to 60.8% across the genetic backgrounds. Hence, the hydration state of this freshly-shed pollen was good. Viability of these pollen samples on Day-0 is listed in Table 1. Five of the eight backgrounds displayed values of 50%, or greater.

Figure 11:
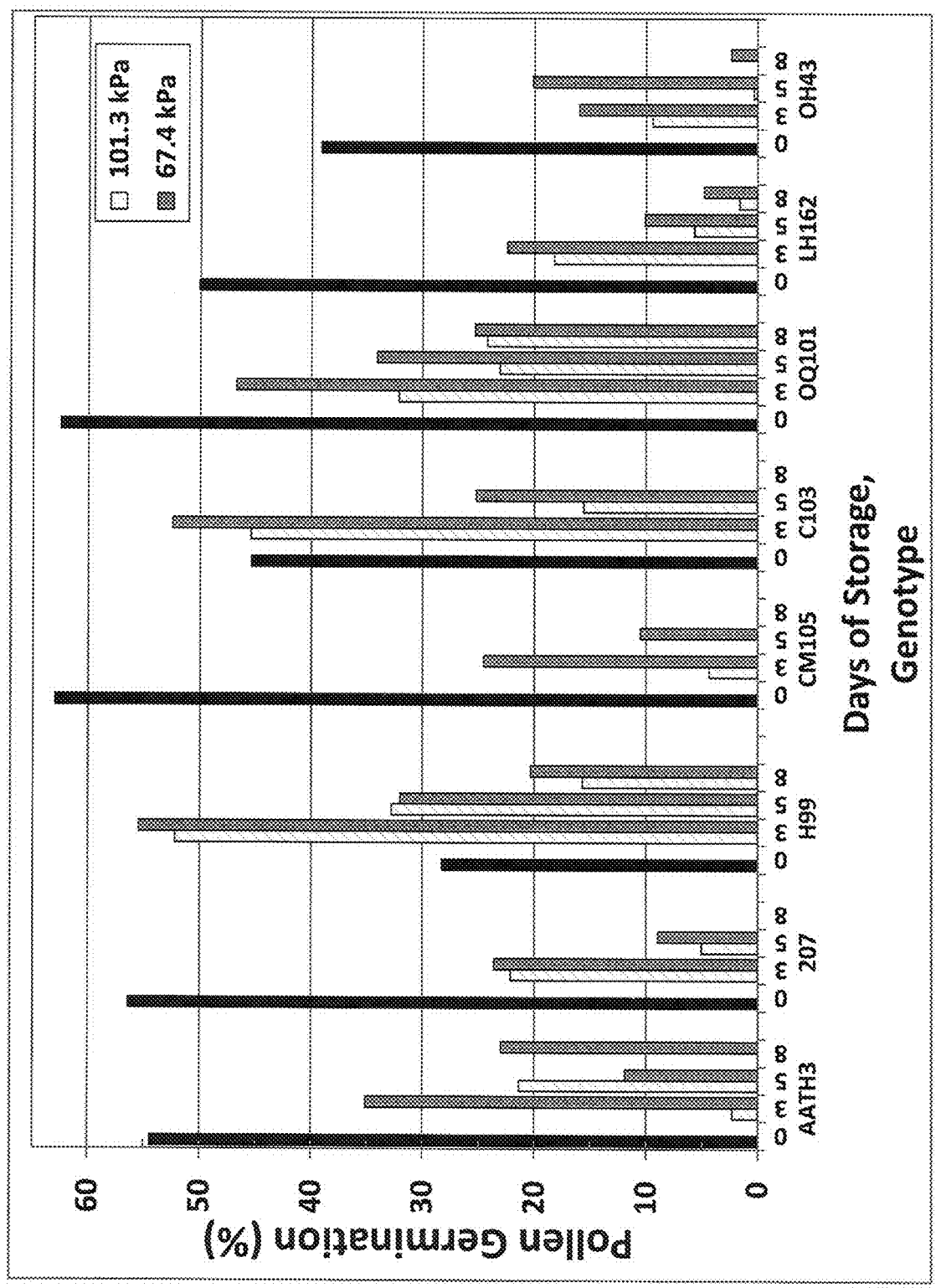
FIG. 11: This figure demonstrates the viability of pollen from eight different genetic backgrounds after field conditioning with high humidity and low temperature at time zero, and then after 3, 5 and 8 days of storage at air pressure values of either 101.3 kPa or 67.4 kPa.

In general, the viability of pollen declined during the eight days of storage (FIG. 11). Deterioration of viability occurred more quickly for some genetic backgrounds (e.g., background "207") than others but, overall, storage under vacuum (67.4 kPa) allowed pollen to maintain a higher viability for each period of preservation. Table 2 shows that, averaged across the eight genetic backgrounds, even after only three days of storage viability was 48% better when pollen was held at reduced pressure. By eight days of storage the advantage of vacuum preservation was 82%, compared to storage at atmospheric pressure. This again demonstrates that the longevity of maize pollen viability, and therefore, fertility, is extended with preservation at reduced pressure and/or oxygen level.

TABLE 2

Average viability of pollen from eight genetic backgrounds stored at atmospheric pressure (101.3 kPa) or under slight vacuum (67.5 kPa).

| Days of Storage | In Vitro Germination (%) | | Percent Improvement with |
|---|---|---|---|
| | Storage at 101.3 kPa | Storage at 67.5 kPa | Storage at 67.5 kPa |
| 3 | 23.3 | 34.5 | 48.4 |
| 5 | 13.0 | 19.1 | 47.1 |
| 8 | 5.2 | 9.5 | 82.5 |

Storage of maize pollen is proven to be better under vacuum. Viability of maize pollen, a member of the Gramineae family, remains at a higher level with vacuum storage compared to storage at atmospheric pressure and the mechanism is quickly functional, within three days, or less. It is best to combine preservation of Gramineae pollen under vacuum with storage at high humidity and low temperature, two other environmental conditions proven to favor pollen viability and reduce its deterioration when held at non-freezing temperatures. Because viability remains higher with maize pollen stored under vacuum, it can be expected that vacuum-stored pollen can be preserved for longer periods of time before loss of viability occurs. Not all levels of vacuum evacuation facilitate extension of pollen viability during storage and, in the case of maize, optimum conditions are approximately 67-84 kPa of pressure. Furthermore, not all genetic forms of maize pollen respond in an identical fashion to vacuum storage and some genetic backgrounds display more, or less, benefit from handling in this manner. Our testing with a wide diversity of maize germplasm and the like favorable response to vacuum storage across the backgrounds, however, indicate that it is reasonable to assume that most, if not all, forms of maize will display improved storage of pollen when stored under pressure of approximately 67-94 kPa. This practice further enables development of commercial services where large quantities of pollen are collected at an initial time, held in controlled environmental conditions for extended periods, and used at a later time to provide supplemental pollination to seed or grain crops for the purpose of improving yield and/or purity.

Example 8: Pollen Field Conditioning: Dehydration Before Storage

This example outlines experiments conducted with dehydration of pollen before storage.

Freshly-shed maize pollen typically has a PMC of about 60% (Fonseca and Westgate (2005) *Field Crops Research* 94: 114-125). The PMC may be lower and the pollen partially dehydrated if the pollen is shed during periods of stress, such as when unfavorable vapor pressure deficit exists (Example 3). Stress commonly compromises pollen viability. In these circumstances, the state of pollen hydration can often be improved and viability revived, either partially or in whole, through field conditioning (Example 4, FIG. 5). But full restoration of PMC and viability to "normal" levels is not always achieved and so it was of interest to investigate how dehydration prior to storage affected pollen viability.

Pollen used in these experiments was sourced from tassels taken from field or greenhouse grown maize. The tassels were detached from plants and transported to the laboratory where 4 cm of each tassel's stem was cut off and discarded. The freshly cut ends of tassels were inserted into a beaker containing water. The tassels were kept in an incubator programmed for 25°/15° C. day/night temperature and 65%/80% day/night relative humidity, as well as daytime lighting. Tassels were acclimated to the incubator environment for at least 24 hours before collection of pollen. Following acclimation, pollen was shaken from freshly-shedding tassels approximately two to four hours after the start of the daytime environmental conditions. The tassels were from a mix of several maize inbred genotypes and one variety of sweet-corn. Although the genetic identity of plants used was known in most cases, no attempt was made to determine the proportional contribution each genotype made in providing a pool of pollen for daily use. Collected pollen was separated from debris by screening (150 micron pore size), immediately placed into field conditioning (Example 1), and held as such for 2-24 hours.

In experiment-A, field conditioned pollen was dehydrated to varying degrees by passing dry nitrogen gas over the pollen at 9° C. The pollen was held on a screen (45 micron pore size) in a small (1.0 L) desiccator and nitrogen continuously streamed through the desiccator in a manner akin to that used by others (Barnabas, B. and Rajki, E. (1981). *Ann Bot,* 48(6), pp. 861-864). Subsamples of pollen were taken from the desiccator at 30 minute intervals, analyzed for viability, and loaded into uncapped 0.5 mL polyethylene microfuge tubes until the tube was approximately 20% full. The tubes were placed in a 3.78 L stainless steel sealed chamber that had a pressure of 67.4 kPa (i.e., vacuum) and was stored at 5° C. The chamber was removed after 6, 9, and 1.7 days of storage to retest viability.

In experiment-B, field conditioned pollen was measured for PMC and viability before being treated with varying conditions of relative humidity. Pollen was spread as a thin layer in aluminum weigh boats (4.3 cm dia.) which were placed on a raised platform in 0.5 L glass storage containers that seal air-tight. The glass containers contained approximately 200 mL, of water or a saturated solution of (ACS reagent grade) potassium sulfate, potassium nitrate, or strontium nitrate which, respectively, produce a calculated relative humidity of 100%, 98.5%, 96.5% or 92.4% in an enclosed container at 5° C. (Greenspan, L., (1977) *J Res Nat Bur Stand,* 81(1), pp. 89-96). The glass containers were stored at 5° C. and opened for less than 20 seconds after 6 and 11 days of incubation to subsample pollen and retest PMC and viability.

Viability in experiments A and B was measured by Impedance Flow Cytometry (IFC) on an Amphasys AG (Lucerne, Switzerland) AmphZ30 instrument. This device singulates pollen grains as they flow through a microfluidic chip supplied with microelectrodes. Changes in the electrical impedance (resistance) of the fluidic medium are measured when cells pass through the applied electric field and discrimination of dead versus live pollen cells is achieved by changes of the phase angle of the detected impedance signal (Heidmann, I., Schade-Kampmann, G, Lambalk, J., Ottiger, M. and Di Berardino, M., 2016. Impedance Flow Cytometry: A Novel Technique in Pollen Analysis. *PloS one,* 11(11), p.e 0165531). Roughly 3,000 pollen grains were measured for each assay. For determination of PMC, samples were handled as described in Example 3.

Figure 12:
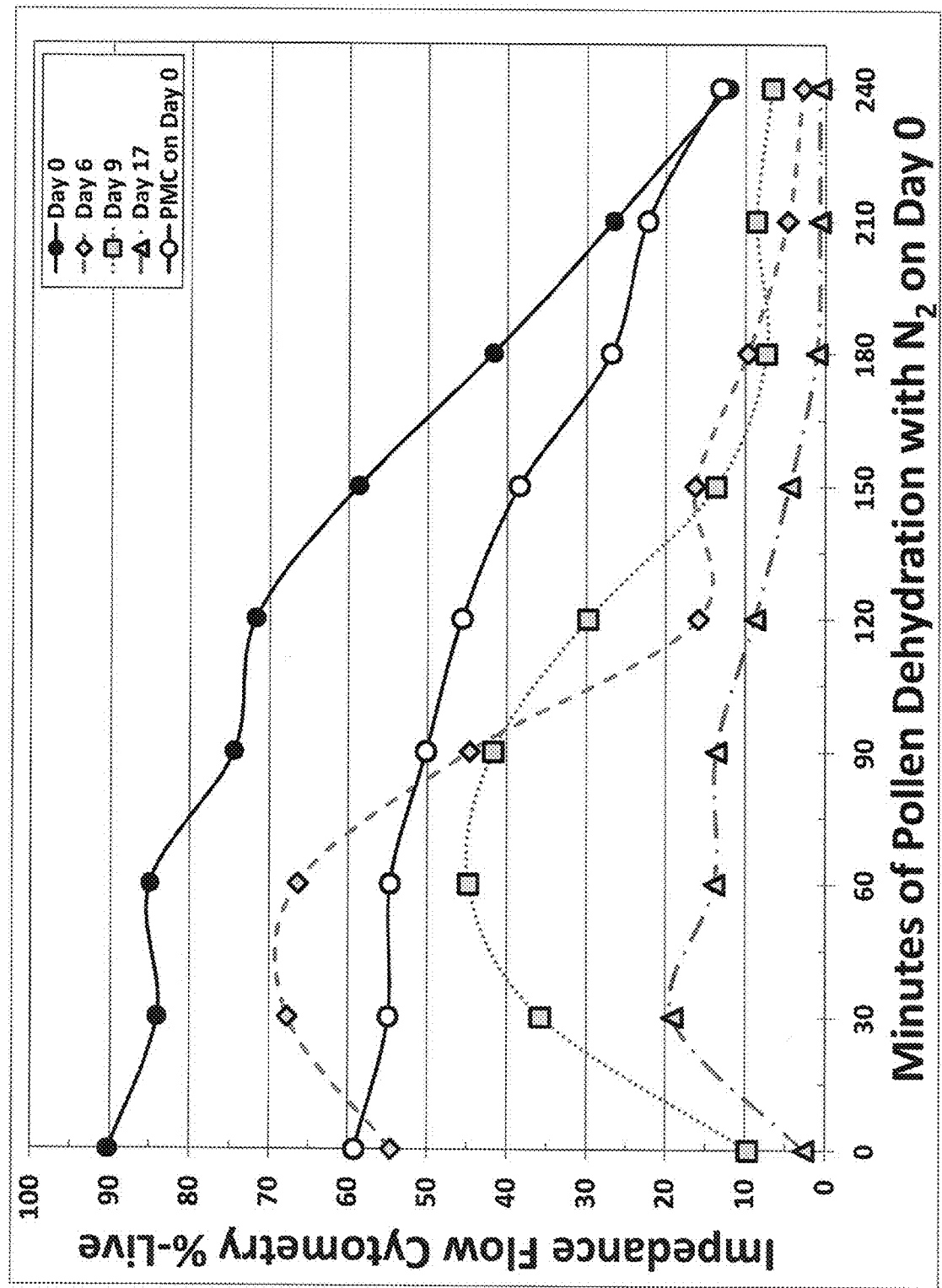
FIG. 12: This figure shows the dehydrating effect of nitrogen gas on pollen moisture content during a four-hour period of exposure and how dehydrating pollen to varying degrees affects its viability when stored for 17 days.

Dehydration of pollen with nitrogen gas in experiment-A caused a steady decline of PMC over a four hour period (FIG. 12). The PMC was 59.2% at the start of dehydration treatment and 13.1% when treatment ended. By midway through dehydration with nitrogen, the PMC had declined to 45.6%.

A subsample of pollen, at each step of dehydration, was placed into low temperature, low pressure storage in a sealed chamber and held there for 17 days. Since no attempt was made to control the level of water vapor in the chamber during storage, it is possible that the subsamples of pollen further dehydrated, or hydrated, during storage. Relative humidity in the sealed chamber was primarily determined by laboratory ambient air conditions at the time the chamber was closed. Laboratory air typically had a relative humidity of about 30% at the time of year experiment-A was conducted.

The rate that pollen subsamples within the storage chamber of experiment-A could have further dehydrated, or hydrated, during storage would also have been affected by the manner of pollen containment within the chamber. The subsamples were stored in the lower portion of a plastic conical tube, so the entire surface area of the pollen was not equally exposed to water vapor in the chamber, like what would have occurred if the samples were spread in a thin stratum.

In experiment-A, the viability of pollen declined over the 17-day storage period, regardless of the initial PMC (FIG. 12). But it was very surprising to see that viability of pollen subsamples, which were dehydrated to 50-55% PMC ahead of storage, deteriorated slower than pollen not dehydrated before storage or pollen dehydrated to PMC levels less than roughly 45%. In fact, pollen only slightly dehydrated before storage, from a PMC of 59.2% for field conditioned pollen to 55.0% after 30 minutes dehydration treatment, still had a 19.1%-Live viability after 17 days of preservation.

Pollen hydration level will normally come to "equilibrium moisture content" (EMC), which is controlled by temperature and relative humidity of the surroundings (Connor, K. F. and Towill, L. E. (1993) *Euphytica*, 68(1), pp. 77-84). Since the rate of viability loss of stored maize pollen was slower in experiment-A than typical, it was reasonable to hypothesize that the stored pollen did not reach EMC with the dry air (30% RH) in the chamber. Perhaps this was because of the pollen's placement in a plastic, conical tube. The notion that only slight dehydration of fresh pollen is needed for best practice of preserving viability of the material was tested in experiment-B.

Maize pollen in experiment-B was stored with the intent of having the PMC at EMC reach approximately 45-55%. This approximates the PMC levels of pollen that remained most viable during storage in experiment-A. Controlled relative humidity levels employed in storage chambers of experiment-B were chosen carefully and employed saturated solutions of potassium sulfate, potassium nitrate, and strontium nitrate (as well as pure water). Hence, the range of relative humidity used as treatment was 92.4-100%. In the past, over more than 100 years, researchers have stored fresh maize pollen at varying levels of humidity and assessed the value of such treatment in extending viability (i.e., storability) during preservation (Andronescu, Demetrius I., The physiology of the pollen of *Zea mays* with special regard to vitality. Thesis for degree of Ph.D. University of Illinois. 1915); (Knowlton, H. E., 1922. *Studies in pollen with special reference to longevity*. (Vol. 52). Cornell University); (Sartoris, G. B., (1942) *Am J Bot, pp.* 395-400); (Jones, M. D. and Newell, L. C., (1948) *J Amer Soc Agron* 40:195-204). Their work taught that storage at high humidity, typically evaluating 90 or 100% humidity, preserves viability of the pollen better than storage at lower humidity. But even with storage at 90 or 100% humidity, viability or fertility of the pollen was only maintained for a few, to 10, days and viability of the samples declined sharply over the period of testing. Never before has it been reported or known that storage and preservation of maize pollen at a relative humidity (e.g., 95-98%) that causes an EMC of about 45-55% is, in fact, a very unique condition of the pollen and one that provides maintenance of viability in storage undisputedly superior to that of storage which produces a greater or lesser PMC.

Figure 13A:
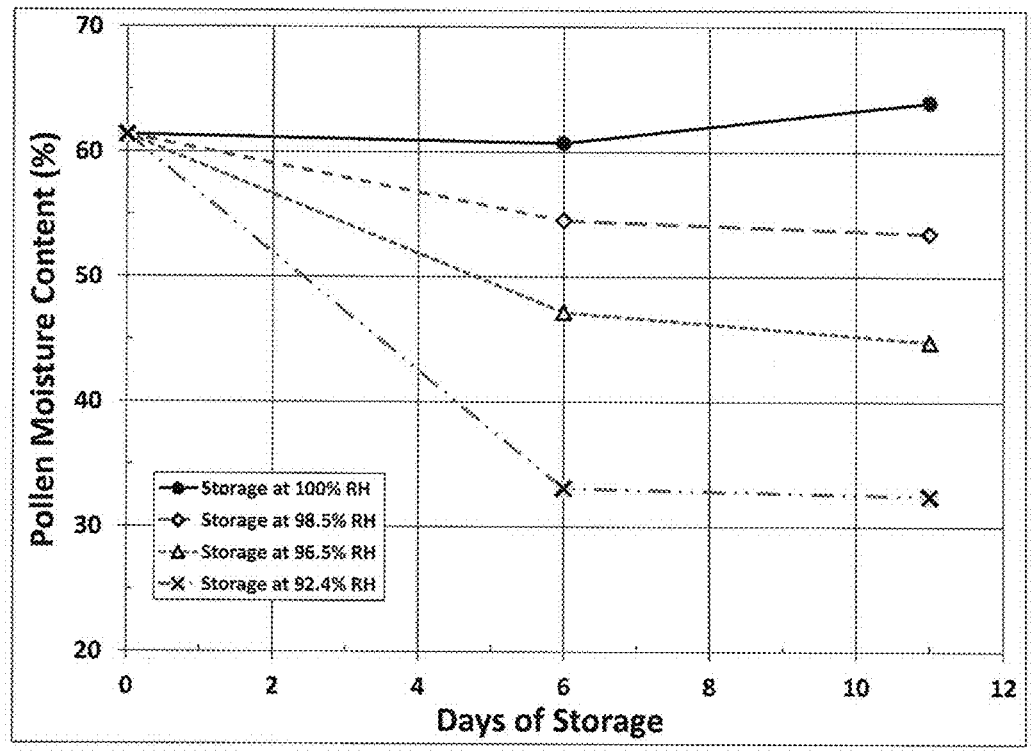
FIGS. 13A and 13B: These figures show the pollen moisture content of pollen stored at varying relative humidity levels over an eleven-day period.
Figure 13B:
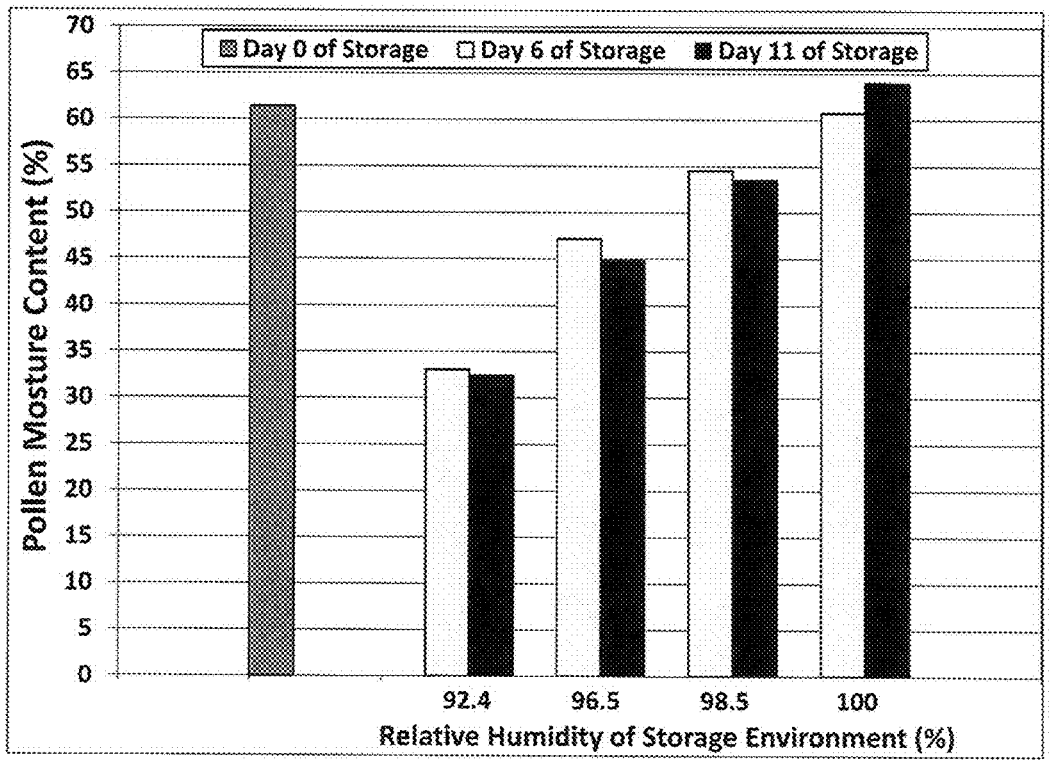
Figure 14A:
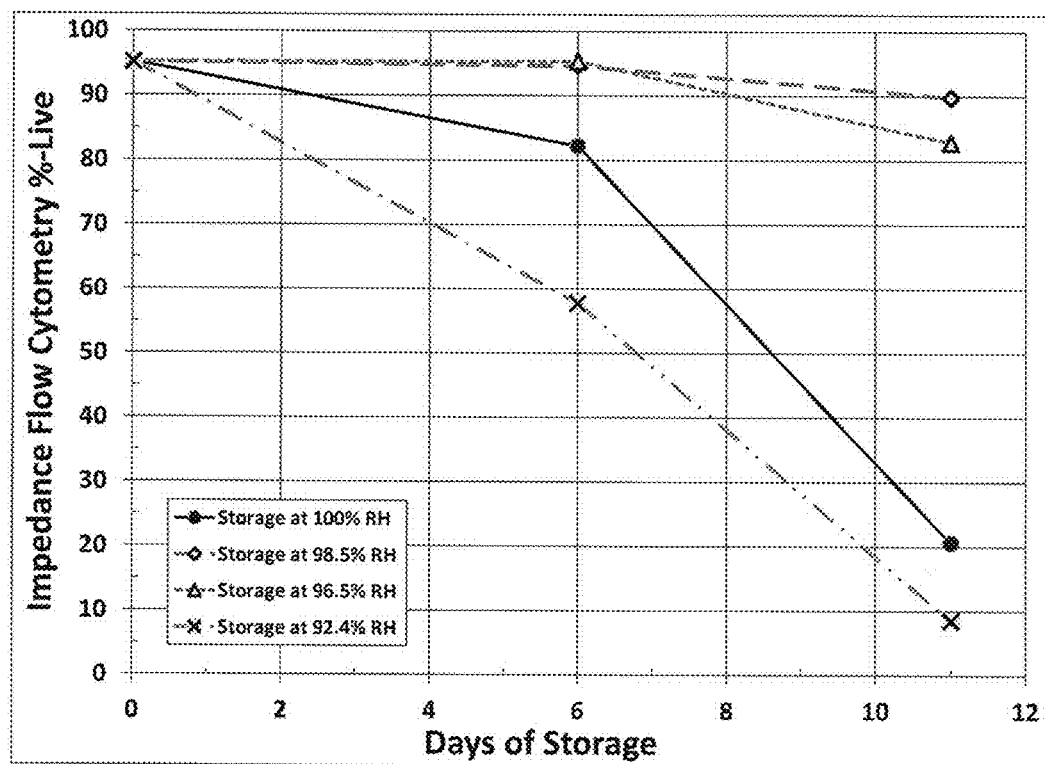
FIGS. 14A and 14B: These figures show the viability of maize pollen stored at varying relative humidity levels over an eleven-day period.
Figure 14B:
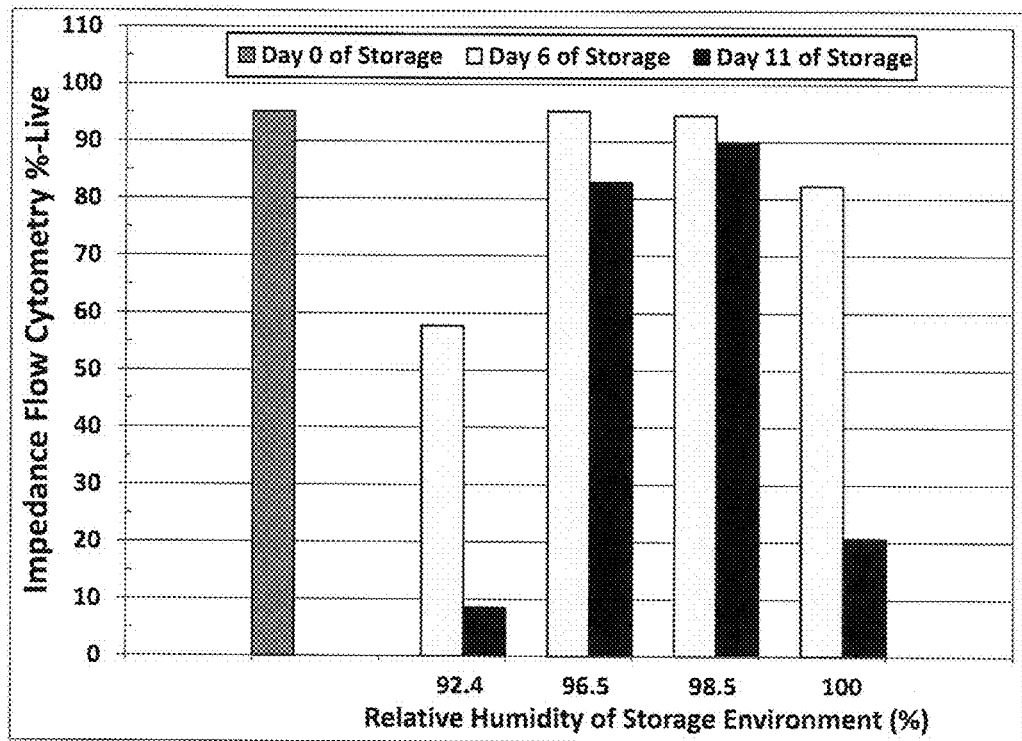

The PMC of pollen stored at varying relative humidity in experiment-B declined in a strict, linear fashion as storage humidity declined (FIGS. 13A and 13B). Little change in PMC occurred beyond six days of storage, meaning the EMC was reached, or nearly so, in that time. Storage at relative humidity of 96.5 and 98.5% produced an equilibrium PMC (i.e., EMC) of 43.8 and 53.5%, respectively, as was targeted. FIGS. 14A and 14B shows that maize pollen stored in conditions of relative humidity that produced an equilibrium PMC of 44 or 54% retained nearly its full viability over an 11-day period of preservation. Pollen stored at 100% or 92.4% relative humidity lost 78 and 91% of its viability, respectively, after 11 days.

It is logical to believe that methods practiced and results obtained in experiment-B provide an understanding of how to extend the viability of maize pollen, without freezing, for extended periods of time that were heretofore unattainable. Even work reported by Nath and Anderson (Nath, J., & Anderson, J. O. (1975). Effect of freezing and freeze-drying on the viability and storage of *Lilium longiflorum* L. and *Zea mays* L. pollen. *Cryobiology*, 12(1), 81-88) failed to prevent deterioration of viability in unfrozen pollen and it's not entirely clear that their observations were based on in vitro pollen germination, as opposed to pseudo-germination (Andronescu, Demetrius I., The physiology of the pollen of *Zea mays* with special regard to vitality. Thesis for degree of Ph.D. University of Illinois. 1915). An ability to maintain the viability of unfrozen pollen in a fashion analogous to that demonstrated in Example 8 further enables practices that aim to preserve Gramineae pollen so that it can be used for pollination and ovule fertilization in a temporal manner precluded by normal periods of receptivity of female inflorescences in crop plants. It can also provide flexibility in the practice of cryopreservation and enhance the quality of pollen intended for such use.

Example 9: Rice Pollen Preservation

In order to validate that the preservation protocol developed for maize is compatible with the pollen from other plant species, testing was conducted using rice as a pollen source.

For the experiment, pollen from 2 different rice genotypes, one from Asia and the other from the southern United States, were collected from actively shedding rice plants and bulked together. Pollen from the bulk was aliquoted into 2 different types of destination vessels. In the first vessel type, a light dusting of pollen was applied across the bottom of two VWR brand 100 mm wide by 15 mm deep petri dishes. The lids to the petri dishes were intentionally left off to allow the pollen to interact with the pollen preservation environment. In the second vessel type, just enough rice pollen was added to a 0.5 mL flip cap tube to fill the rounded area at the bottom of the tube. This pollen volume was estimated at 5 µL in each tube. The lids to the tubes were closed after adding the pollen. With the lids in the closed position, the temperature in the tube could be changed, but the relative humidity could not be changed.

Each pollen preservation vessel was placed into an 887 mL Rubbermaid storage container with a sealable lid. Enough $H_2O$ was added to fill the bottom of each Rubbermaid container prior to sealing the container.

Each sealed Rubbermaid container was placed into a 4° C. environment for a preservation period of 20 hours. The pollen preservation vessels received one of two treatments. In treatment 1, the petri dishes were treated at 4° C. with 100% relative humidity for 20 hours. In treatment 2, the 0.5 mL flip cap tubes were treated at 4° C. for 20 hours. After 20 hours of storage, each sample of pollen was placed in a germination media which allows the pollen tube to grow if the pollen is viable. After 60 minutes of time in the media, images were captured. Each image was scored for number of pollen tubes relative to the overall number of pollen grains present.

Results: Rice pollen stored in the petri dishes showed an overall germination rate of 25% and 1% respectively after 20 hours of storage at 4C and 100% relative humidity. The inventors have speculated that the seal on the Rubbermaid vessel which yielded 1% germination was not properly sealed. Failure to seal properly would result in the actual humidity in the vessel to fall well below the 100% total.

Figure 15:
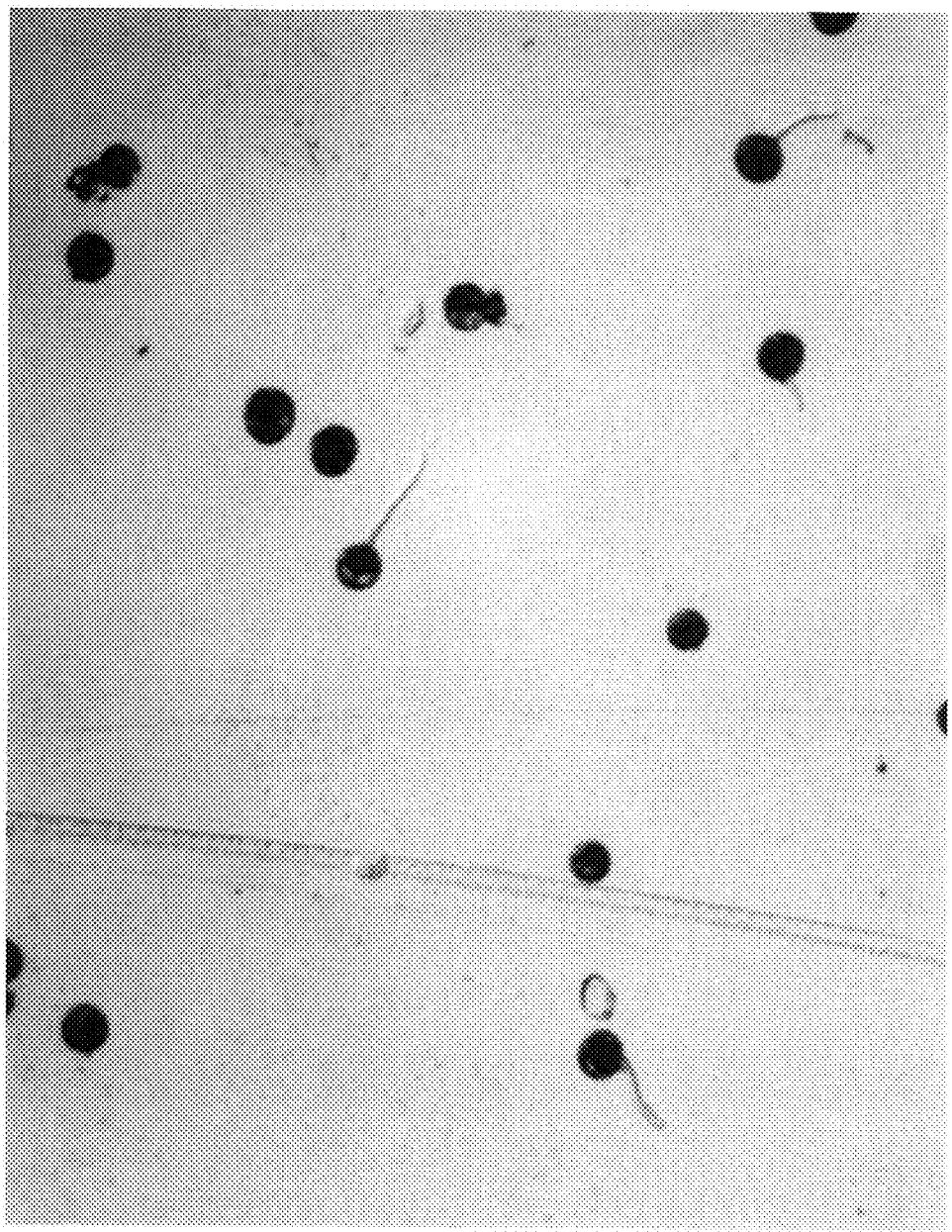
FIG. 15: This figure shows an image of rice pollen stored at 4° C. and 100% relative humidity germinating in culture after 20 hours of preservation.
Figure 16:
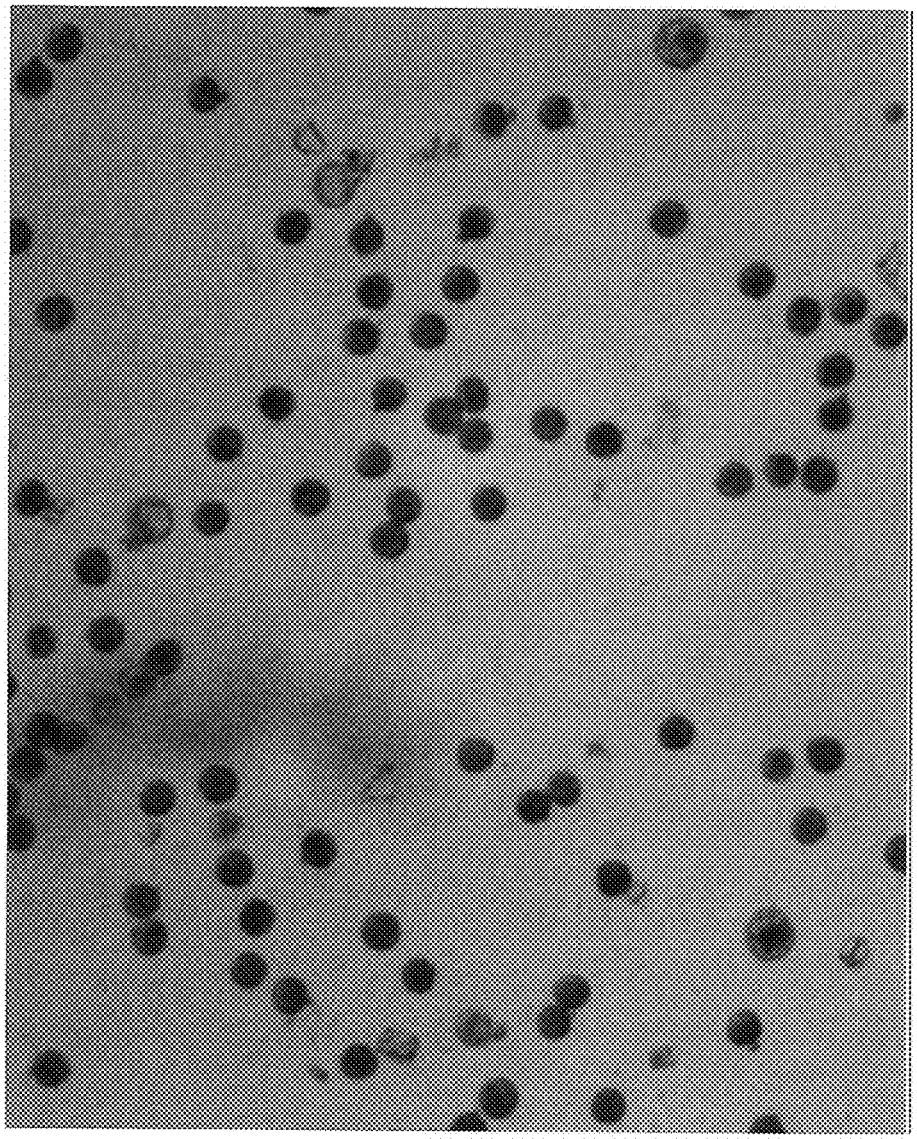
FIG. 16: An image of rice pollen stored at 4° C. without relative humidity control germinating in culture after 20 hours of preservation. Overall germination for this treatment was measured at 1%.

Rice pollen stored in the flip cap tubes showed an overall germination rate of less than 1% after 20 hours of storage at 4C, and no control of relative humidity. It should be noted that this germination percent is consistent with the petri dish pollen stored at 4° C. and 100% relative humidity germinating in culture after 20 hours of preservation that yielded 1% germination as both scenarios would reflect an environment that fail to keep humidity near 100%. FIG. 15 provides an image of the germinated rice from the petri dish having a germination rate of 25%, while FIG. 16 provides an image of rice pollen stored at 4° C. without relative humidity control.

Example 10: Maize Pollen Preservation Using 75% Humidity and Positive Air Flow

This example outlines experiments conducted to prepare pollen for preservation. Pollen used in these experiments was sourced from tassels taken from field and greenhouse grown maize. The tassels were detached from plants and transported to the laboratory where 4 cm of each tassel's stem was cut off and discarded. The freshly cut ends of tassels were inserted into a beaker containing water. The tassels were kept in an incubator programmed for 25°/15° C. day/night temperature and 65%/80% day/night relative humidity, as well as daytime lighting. Tassels were acclimated to the incubator environment for at least 24 hours before collection of pollen. Following acclimation, pollen was shaken from freshly-shedding tassels approximately two to four hours after the start of the daytime environmental conditions. Across all experiments, tassels were from 21 different maize inbred and hybrid genotypes (total of 21 genotypes). Collected pollen from each genotype was maintained and identified by genotype as separate pollen samples. Each pollen sample was separated from debris by screening (150 micron pore size).

After collection of pollen, each sample was immediately sub-sampled and measured (time 0) for viability using amphasys, which is discussed in detail above. Initial viability readings confirmed that all pollen samples had high initial viability of greater than 60%. The remaining pollen for each sample was then placed on a forced air drying apparatus with approximately 75% humidity (enabled by a saturated NaCl solution) at 5° C. and dried for approximately 20 hours. The samples were stored at −80° C. for time periods ranging from 4 hours to 38 days and counting. There was great variation in storage time due to the fact that there were a limited number of females available in the greenhouse to use for cross-pollinations with the stored pollen on any given day, and therefore several of the samples had to wait in −80° C. conditions until a female was available.

Samples were removed from the −80° C. storage conditions, placed on dry ice and transported to the greenhouse to make pollinations. Only properly shoot-bagged ears were used as females to avoid any risk of escapes. Two to three weeks after pollination, the ears were observed to determine if kernels had formed, indicating that the pollen was viable after receiving the treatment described above. Pollen from 18 of the 21 genotypes tested resulted in kernels being formed, indicating that the pollen was still viable after storage at −80° C.

Figure 17A:
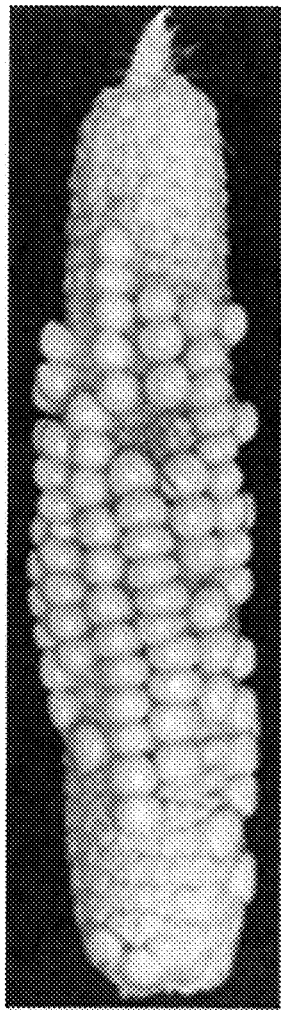
FIGS. 17A, 17B, and 17C show the results of pollinations conducted with preserved pollen following storage periods of 4 hours to 38 days as indicated in example 10 and Table 3.
Figure 17B:
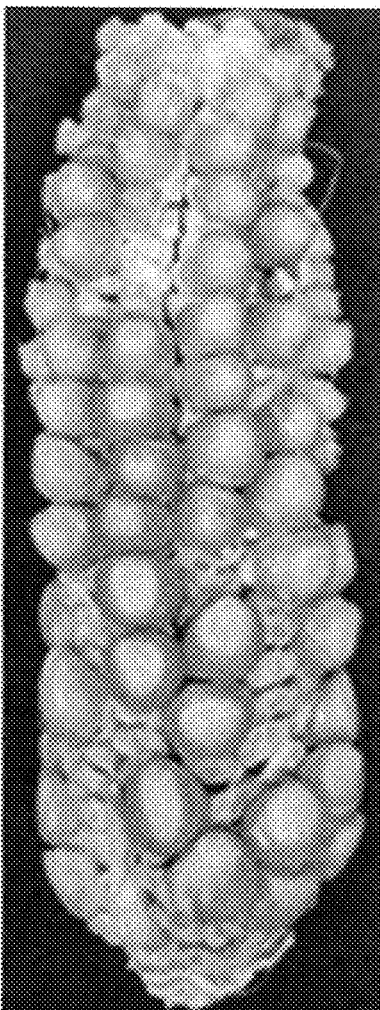
Figure 17C:
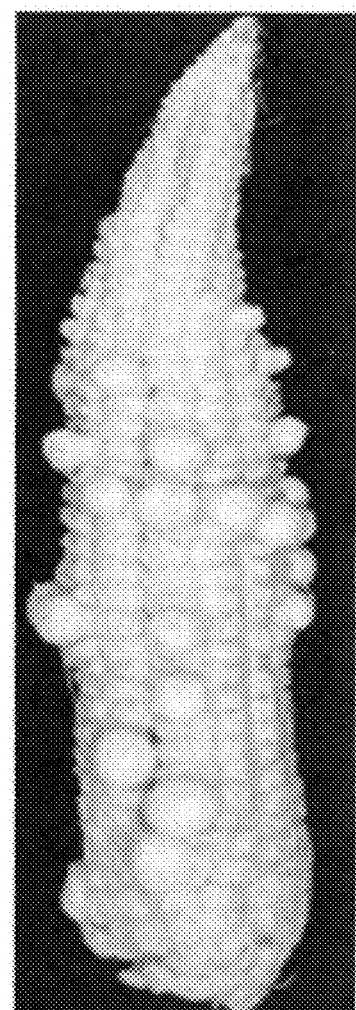

FIGS. 17A, 17B, and 17C provides examples of confirmed viability of preserved pollen stored at −80° C. Specifically, the photographs shown in FIGS. 17A, 17B, and 17C reflect the results of pollinations conducted with preserved pollen following storage periods of 4 hours to 38 days. The presence of developing kernels was assessed two to three weeks after pollination or at kernel maturity, as shown in Table 3 below.

TABLE 3

Presence of developing kernels for example 10 wherein genotype indicates the source of pollen and female indicates the inbred pollinated by the preserved pollen.

| Figure | 16A | 16B | 16C |
| --- | --- | --- | --- |
| Days Pollen Stored at −80° C. | 1 | 1 | 38 |
| Female | 78 | H99 | H99 |
| Age of Kernels (DAP) | 21 | 69 | 19 |

Example 11: Maize Pollen Preservation Using Nitrogen Gas and Positive Pressure

This example outlines an experiment conducted to prepare pollen for preservation. Pollen used in this experiment was sourced from tassels taken from the field. The tassels from a single sweetcorn hybrid were detached and transported to the laboratory where 4 cm of each tassel's stem was cut off and discarded. The freshly cut ends of tassels were inserted into a beaker containing water. The tassels were kept in an incubator programmed for 25°/15° C. day/night temperature and 65%/80% day/night relative humidity, as well as daytime lighting. Tassels were acclimated to the incubator environment for at least 24 hours before collection of pollen. Following acclimation, pollen was shaken from freshly-shedding tassels approximately two to four hours after the start of the daytime environmental conditions. Pollen samples were separated from debris by screening (150 micron pore size).

After collection of pollen, a sub-sample was measured (time 0) for viability using amphasys as described above, which confirmed that the pollen had high initial viability of greater than 95%. The remaining sample was then placed on a forced nitrogen drying apparatus at 5-10° C. (temperature varied). The nitrogen gas served the dual purpose of depleting the environment of oxygen while also decreasing the humidity. Relative humidity varied during drying from 40% at time 0 to 12% after 110 minutes. Three sub-samples of pollen were removed at 80, 85, 90, 95, 100, and 110 minutes. The first sub-sample was used to measure pollen moisture content (PMC) of the sample. This PMC is reported in Table 4. The second sub-sample was used to measure pollen viability before freezing. The third sub-sample was stored at −80° C. for 120 minutes and used to measure pollen viability after freezing. Table 4 shows percent viability of the pollen used in this experiment. Results show that there is a range of PMCs from 15 to 35 in which pollen is more stable and can be stored more effectively while minimizing the drop in viability.

TABLE 4

Percent viability for pollen dried to different percent moisture content (PMC).

| Sample | Time on dryer (min) | Humidity reading (%) | PMC (%) | % viable before freeze | % viable after freeze | % drop in viability |
|---|---|---|---|---|---|---|
| 201-1 | 0 | 40 | 64.4 | 97.1 | 28.2 | 71.0 |
| 201-2 | 80 | 27 | 35.0 | 67.4 | 28.6 | 57.6 |
| 201-3 | 85 | 26 | 31.1 | 71.6 | 37.1 | 48.2 |
| 201-4 | 90 | 21 | 28.5 | 70.7 | 24.7 | 65.1 |
| 201-5 | 95 | 19 | 24.1 | 34.0 | 18.0 | 47.1 |
| 201-6 | 100 | 17 | 19.1 | 53.6 | 15.9 | 70.3 |
| 201-7 | 110 | 12 | 17.4 | 31.7 | 5.7 | 82.0 |

Example 12. Maize Pollen Preserved Using Nitrogen Gas, Positive Pressure, and Adjustable Humidity and Temperature Pollen that has been collected from actively shedding plants is placed into the preservation chamber. A constant flow of nitrogen gas flows to the chamber. The nitrogen gas serves the dual purpose of depleting the environment of oxygen, which is required for metabolism to occur, while also decreasing the humidity, which accordingly begins reducing the pollen moisture content to low levels, such as a target level of about 30%. As the pollen moisture content decreases, the temperature in the chamber can slowly be adjusted down to well below 0° C. (−5° C. for example) without freezing the pollen. Similarly, the relative humidity levels in the chamber can also be adjusted to increase or decrease the rate of pollen dehydration. Concomitantly, the humidity in the chamber can also be adjusted up to stabilize the final pollen moisture content at about 30%. Using $PV=nRT$, a final humidity value can be calculated to hold the preserved pollen at an equilibrium pollen moisture content of 30%. This process can be accomplished in approximately 100 minutes.

Example 13. Maize Pollen Preserved in Liquid Nitrogen

To test the potential of using maize pollen that has been rapidly frozen as a source of preserved pollen, an experiment was conducted to determine what percent of maize pollen survives after being flash frozen in liquid nitrogen. According to Nath and Anderson (Nath, J., & Anderson, J. O. (1975). Effect of freezing and freeze-drying on the viability and storage of *Lilium longiflorum* L. and *Zea mays* L. pollen. *Cryobiology*, 12(1), 81-88), "Rapid freezing of pollen at rates of approximately 200 degrees C./min maintains the highest degree of viable pollen in combination with rapid thawing rates of 218" C/min. Rapid cooling and slow rewarming resulted in a substantial loss of pollen viability. This might indicate that intracellular ice crystals formed during rapid cooling perhaps grow into larger ice masses during slow rewarming or storage at temperatures above −50° C."

For the experiment, maize pollen was collected from several different actively shedding genotypes and bulked into a single source tube. To achieve a rapid freeze of the pollen, 50 mL of liquid nitrogen was poured into a 100 mL borosilicate beaker. The fresh pollen was then dropped into the liquid nitrogen to achieve the rapid freeze. The pollen remained in the liquid nitrogen until the entire 50 mL volume had boiled away. The rapidly frozen pollen was immediately added to room temperature maize pollen germination media to achieve a rapid thaw rate of the pollen.

Figure 18:
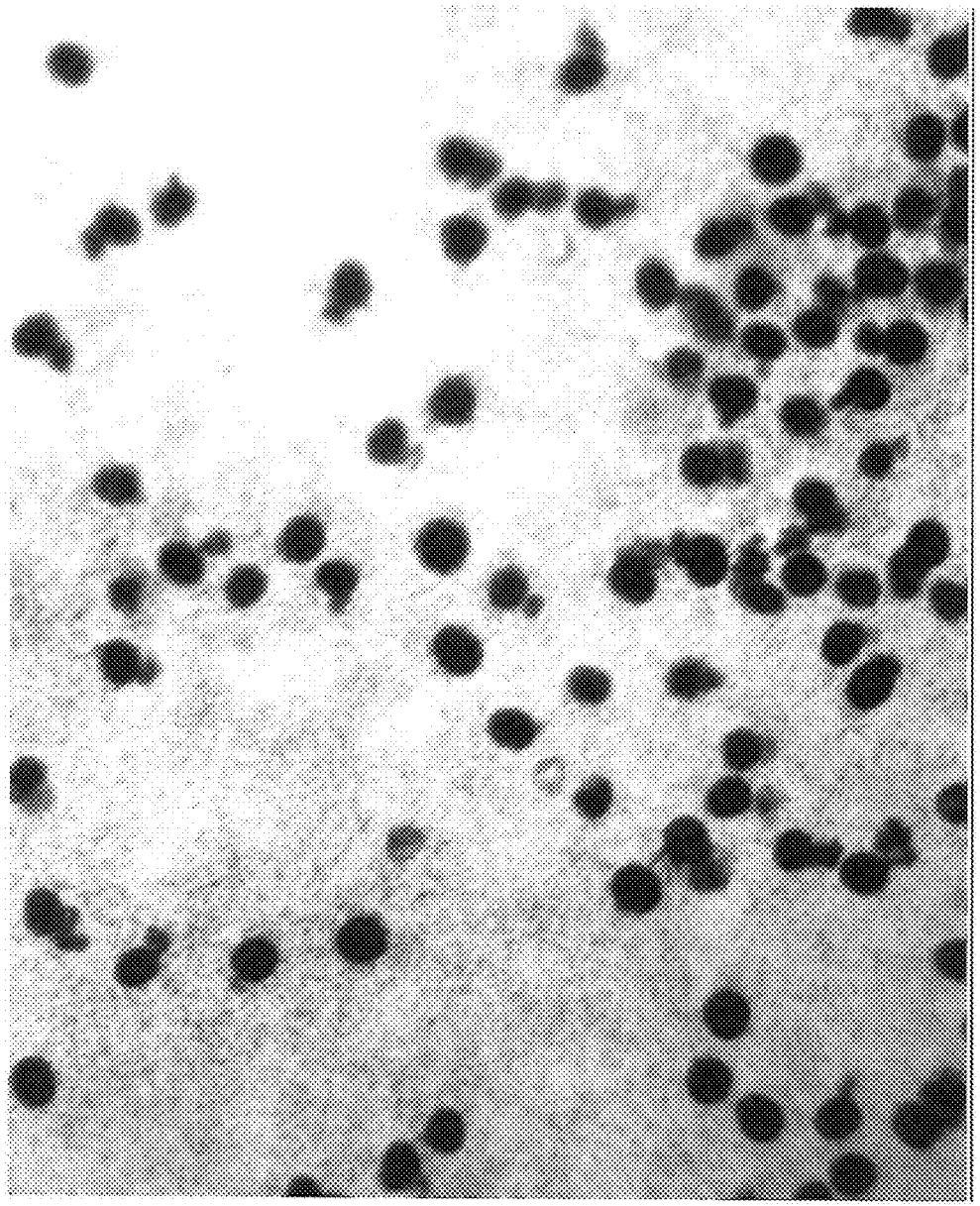
FIG. 18: This figure shows the final germination media results from rapidly frozen and rapidly thawed maize pollen. Overall germination was scored at less than 0.5%.

The results of the germination test were captured in images which were subsequently scored for percent pollen tube growth compared to overall number of pollen grains. The vast majority of the pollen rapidly degraded during the pollen tube germination assay. Significant leakage of the cellular contents was noted as a large amount of debris became evident in the media during the germination process. The final germination rate was scored at 1/221 grains of pollen, or less than 0.5%. FIG. 18 shows the final germination media results from the above-described rapidly frozen and rapidly thawed maize pollen. Overall germination was scored at less than 0.5%.

Accordingly, as provided in the above, the methods of the present invention provide a number of advantages which have heretofore been lacking in the industry. The present invention provides large scale pollen preservation methods. The methods of the present invention maintain and increase pollen viability during collection, as well as during preservation. Moreover, the methods of the present invention are applicable to, but not limited to, two specific advantageous situations. First, the method is applicable to instances where pollen will be used within 30 days of collection in support of the current growth cycle at the time of collection. Second, the invention allows indefinite storage duration, which allows for pollen to be stored for years prior to delivery as desired to receptive female plants.

Furthermore, the majority of prior pollen preservation methods rely on freezing and subsequent freeze drying of the pollen (including, but not limited to, the Greaves, et al. and Nath and Anderson methods described above) to achieve dehydration of pollen to conditions wherein the pollen may be stored. However, the lengthy time necessary to freeze dry the pollen reduces the amount of time wherein the pollen may be used for field applications. Further, the methods of the prior art do not control the pollen moisture content, which in some embodiments may be important to preserving the pollen. Failure to fall within the sensitive pollen moisture content range which allows pollen to be preserved results in significant loss of viability. Moreover, the pressure requirements of the present invention allow for increased scalability and portability over methods of the prior art, which require more extreme pressure conditions. Methods of the current invention provide for quick dehydration of pollen and also enables the pollen to be held at the optimum pollen moisture content.

Although various representative embodiments of this invention have been described above with a certain degree of particularity, those skilled in the art could make numerous alterations to the disclosed embodiments without departing from the spirit or scope of the inventive subject matter set forth in the specification and claims. In some instances, in methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

Although the present invention has been described with reference to the embodiments outlined above, various alternatives, modifications, variations, improvements and/or substantial equivalents, whether known or that are or may be presently foreseen, may become apparent to those having at least ordinary skill in the art. Listing the steps of a method in a certain order does not constitute any limitation on the order of the steps of the method. Accordingly, the embodiments of the invention set forth above are intended to be illustrative, not limiting. Persons skilled in the art will recognize that changes may be made in form and detail without departing from the spirit and scope of the invention. Therefore, the invention is intended to embrace all known or earlier developed alternatives, modifications, variations, improvements, and/or substantial equivalents.

The invention claimed is:

1. A method of preserving pollen from cereal crops comprising:
    (a) collecting pollen and/or anthers
    (b) subjecting the pollen and/or anthers to preservation conditions including:
        (i) a temperature ranging from about −10° C. to about 10° C.,
        (ii) an air flow at a humidity of 0% to about 99%, wherein the air pressure is capable of adjustment from 15 kPa to 150 kPa and the pollen is dehydrated until the pollen moisture content reaches about 15% to about 35%, and
    (c) storing the pollen and/or anthers for future use.

2. The method of claim 1 wherein the air flow includes a flow of one or more continuously refreshed, selected gases.

3. The method of claim 2 wherein the selected gas is nitrogen gas and the concentration of the nitrogen gas is about 78% to about 100%.

4. The method of claim 1 wherein the air flow humidity level is controlled by using:
    (a) a saturated salt solution;
    (b) a two-pressure process;
    (c) a two-temperature process; or
    (d) one or more apparatus selected from the group consisting of:
        (i) a dew-point generator;
        (ii) an atomizer;
        (iii) a mixed-flow generator; and
        (iv) a sonicator.

5. The method of claim 1 wherein the pollen and/or anthers are freshly collected from actively shedding plants.

6. The method of claim 1 wherein the pollen and/or anthers have been previously collected and stored.

7. The method of claim 1 wherein the pollen is collected from the anthers by crushing, grinding, or otherwise disrupting the anther in order to obtain the pollen therefrom.

8. The method of claim 1 wherein said pollen and/or anthers are selected from the group consisting of maize, rice, and wheat.

9. The method of claim 1 wherein said pollen and/or anthers are maize pollen and/or anthers.

10. The method of claim 1 wherein the step of storing the pollen and/or anthers for future use comprises storing the pollen and/or anthers at a temperature ranging from −80° C. to −30° C.

11. The method of claim 1 wherein the step of storing the pollen and/or anthers for future use comprises storing the pollen and/or anthers at a temperature ranging from −30° C. to −10° C.

12. The method of claim 1 wherein the step of storing the pollen and/or anthers for future use comprises storing the pollen and/or anthers at a temperature ranging from −10° C. to 10° C.

13. A method of preserving pollen from cereal crops comprising:
    (a) collecting pollen and/or anthers;
    (b) subjecting the pollen and/or anthers to preservation conditions including:
        (i) a temperature ranging from about −10° C. to about 10° C.,
        (ii) a flow of nitrogen at a humidity of 0% to about 99%, wherein the humidity is capable of adjustment and wherein the air pressure is capable of adjustment from 15 kPa to 150 kPa and the pollen is dehydrated until the pollen moisture content reaches about 15% to about 35%, and
    (c) storing the pollen and/or anthers for future use.

14. The method of claim 13 wherein the nitrogen flow humidity level is controlled by using:
    (a) a saturated salt solution;
    (b) a two-pressure process;
    (c) a two-temperature process; or
    (d) one or more apparatus selected from the group consisting of:
        (i) a dew-point generator;
        (ii) an atomizer;
        (iii) a mixed-flow generator; and
        (iv) a sonicator.

15. The method of claim 13 wherein the pollen and/or anthers are freshly collected from actively shedding plants.

16. The method of claim 13 wherein the pollen and/or anthers have been previously collected and stored.

17. The method of claim 13 wherein the fresh pollen is collected from the anthers by crushing, grinding, or otherwise disrupting the anther in order to obtain the pollen therefrom.

18. The method of claim 13 wherein said pollen and/or anthers are selected from the group consisting of maize, rice, and wheat.

19. The method of claim 13 wherein said pollen and/or anthers are maize pollen and/or anthers.

20. The method of claim 13 wherein the step of storing the pollen and/or anthers for future use comprises storing the pollen and/or anthers at a temperature ranging from −80° C. to −30° C.

21. The method of claim 13 wherein the step of storing the pollen and/or anthers for future use comprises storing the pollen and/or anthers at a temperature ranging from −30° C. to −10° C.

22. The method of claim 13 wherein the step of storing the pollen and/or anthers for future use comprises storing the pollen and/or anthers at a temperature ranging from −10° C. to 10° C.

* * * * *